(12) United States Patent
Govaerts et al.

(10) Patent No.: US 8,629,144 B2
(45) Date of Patent: Jan. 14, 2014

(54) POLYMORPHIC AND HYDRATE FORMS, SALTS AND PROCESS FOR PREPARING 6-{DIFLUORO[6-(1-METHYL-1H-PYRAZOL-4-YL)[1,2,4]TRIAZOLO[4,3-B]PYRIDAZIN-3-YL]METHYL}QUINOLINE

(75) Inventors: Tom Cornelis Hortense Govaerts, Betekom (BE); Johan Erwin Edmond Weerts, Beerse (BE); Carina Leys, Stabroek (BE); Julius Walter Jozef Dickens, Beerse (BE); Sigrid Carl Maria Stokbroekx, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 438 days.

(21) Appl. No.: 12/665,192

(22) PCT Filed: Jun. 19, 2008

(86) PCT No.: PCT/EP2008/057772
§ 371 (c)(1),
(2), (4) Date: Dec. 17, 2009

(87) PCT Pub. No.: WO2008/155378
PCT Pub. Date: Dec. 24, 2008

(65) Prior Publication Data
US 2010/0197912 A1 Aug. 5, 2010

Related U.S. Application Data

(60) Provisional application No. 60/945,641, filed on Jun. 22, 2007.

(30) Foreign Application Priority Data

Jun. 21, 2007 (EP) .................................... 07012176

(51) Int. Cl.
*A61K 31/50* (2006.01)

(52) U.S. Cl.
USPC .................. 514/252.06; 514/252.05; 544/236

(58) Field of Classification Search
USPC .......................... 544/236; 514/252.05, 252.06
See application file for complete search history.

(56) References Cited

U.S. PATENT DOCUMENTS

| | | |
|---|---|---|
| 5,474,765 A | 12/1995 | Thorpe |
| 5,762,918 A | 6/1998 | Thorpe |
| 5,855,866 A | 1/1999 | Thorpe et al. |
| 6,342,219 B1 | 1/2002 | Thorpe et al. |
| 6,776,796 B2 | 8/2004 | Falotico et al. |
| 2002/0016625 A1 | 2/2002 | Falotico et al. |

FOREIGN PATENT DOCUMENTS

| | | |
|---|---|---|
| WO | 9632907 | 10/1996 |
| WO | WO 2005/004607 | 1/2005 |
| WO | WO 2005/010005 | 2/2005 |
| WO | WO 2007/075567 | 7/2007 |

OTHER PUBLICATIONS

Vippagunta et al., "Crystalline Solids", Adv. Drug Del. Rev., 48 (2001) 3-26.*
Taher, E.I. et al., "Hepatocyte Growth Factor Triggers Signaling Cascades Mediating Vascular Smooth Muscle Cell Migration". *Biochemical and Biophysical Research Communications*, 298 (2002) pp. 80-86.
Schiele, T.M. et al., "Vascular Restenosis-Striving for Therapy". *Expert Opinion Pharmacotherapy*, (2004) 5 (11) pp. 2221-2232.
Simpson, William G., "The Calcium Channel Blocker Verapamil and Cancer Chemotherapy". *Cell Calcium*, 6, 1985, pp. 449-467.
Lal, G.S. et al., "Bis(2-methoxyethyl)aminosulfur Trifluoride: A New Broad-Spectrum Deoxofluorinating Agent with Enhanced Thermal Stability". *J. Org. Chemistry*, (1999), 64, pp. 7048-7054.
Xu, G. et al., "Development of Building Blocks for the synthesis of N-Heterocyclic Carbene Ligands". *Organic Letters*, (2005) vol. 7, No. 21, pp. 4605-4608.
O'Brien, C.J. et al., "Easily Prepared Air-and Moisture-Stable Pd-NHC (NHC=N-Heterocyclic Carbene) Complexes: A Reliable, User-Friendly, Highly Active Palladium Precatalyst for the Suzuki-Miyaura Reaction". *Chemistry European Journal*, (2006), 12, pp. 4743-4748.
Negishi, E., et al., Selective Carbon-Carbon Bond Formation via Transistion Metal Caralysis, 3, A Highly Selective Synthesis of Unsymmetrical Biaryls and Diarylmethans by the Selective Synthesis of Unsymmetrical Biaryls and Diarylmethanes by the Nickel-or Palladium-Catalyzed Reaction of Aryl-and Benzylzinc Derivatives with Aryl Halides. *J. Org. Chemistry*, vol. 42, No. 42, No. 10, (1977) pp. 1821-1823.
Albright, J.D. et al., "Synthesis and Anxiolytic Activity of 6-(Substituted-phenyl0-1,2,4-triazolo{4,3-b]pyridazines". *Journal Med. Chem.* (1981) 24, 5, pp. 592-600.
Park, M. et al., "Sequence of MET Protooncogene cDNA has Features Characteristic of the Tyrosine Kinase Family of Growth-Factor Receptors". *Proc. Natl. Acad. Sci*, USA, vol. 84, Sep. 1987 pp. 6379-6383.
Michieli, P. et al., "Targeting the Tumor and its Microenvironment by a Dual-Function Decoy Met Receptor". *Cancer Cells*, Jul. 2004, vol. 6, pp. 61-73.

(Continued)

*Primary Examiner* — Paul V. Ward

(57) ABSTRACT

The invention relates to novel polymorphic and hydrate forms and salts of 6-{difluoro[6-(1-methyl-1H-pyrazol-4-yl)[1,2,4]triazolo[4,3-b]pyridazin-3-yl]methyl}quinoline, to methods for their preparation, to pharmaceutical compositions comprising at least one of said polymorphic or hydrate forms or salts, and to the therapeutic and/or prophylactic use of such compositions. The invention also provides new manners for preparing said compound.

19 Claims, 12 Drawing Sheets

(56) References Cited

OTHER PUBLICATIONS

Stille, J.K. "The Palladium-Catalyzed Cross-Coupling Reactions of Organotin Reagents with Organic Electrophiles". *Angew. Chem. Int. Ed. English* 25 (1986) pp. 508-524.

Hellstrom, K. et al., "Antibodies for Drug Delivery, Controlled Drug Delivery". *Marcel Dekker, Inc.*pp. 623-653 (1987).

Thorpe, P.E. "Antibody Carriers of Cytotoxic Agents in Cancer Therapy: A Review". *Monoclonal Antibodies*, pp. 475-514 (1984).

Fustero, S. et al. "1,4-Benzodiazepine N-Nitrosoamidines: Useful Intermediates in the Synthesis of Tricyclic Benzodiazepines". *Molecules* (2006), vol. 11, pp. 583-588, ISSN 1420-3049.

Shin Jikken Kagaku Koza. "*Synthesis and Reaction of Organic Compound*", vol. IV, p. 2231, (1978).

\* cited by examiner

POLYMORPHIC AND HYDRATE FORMS, SALTS AND PROCESS FOR PREPARING 6-{DIFLUORO[6-(1-METHYL-1H-PYRAZOL-4-YL)[1,2,4]TRIAZOLO[4,3-B]PYRIDAZIN-3-YL]METHYL}QUINOLINE

CROSS REFERENCE TO RELATED APPLICATIONS

This application is the national stage of PCT Application No. PCT/EP2008/057772filed Jun. 19, 2008, which claims priority from European Patent Application No. 07012176.9, filed Jun. 21, 2007 and U.S. Patent Application No. 60/945,641 filed Jun. 22, 2007, the entire disclosures of all of which are hereby incorporated in their entirety.

FIELD OF THE INVENTION

The invention relates to novel polymorphic and hydrate forms and salts of 6-{difluoro[6-(1-methyl-1H-pyrazol-4-yl)[1,2,4]triazolo[4,3-b]pyridazin-3-yl]methyl}quinoline (compound (I)), to methods for their preparation, to pharmaceutical compositions comprising at least one of said polymorphic or hydrate forms or salts, and to the therapeutic and/or prophylactic use of such compositions. The invention also provides new manners for preparing the compound (I).

BACKGROUND OF THE INVENTION

The compound 6-{difluoro[6-(1-methyl-1H-pyrazol-4-yl)[1,2,4]triazolo[4,3-b]pyridazin-3-yl]methyl}quinoline (compound (I) herein) is disclosed in co-pending application PCT/US2006/048241 published as WO 2007/075567. Compound (I) is a protein tyrosine kinase modulator, particularly inhibitor of c-Met.

The hepatocyte growth factor (HGF) (also known as scatter factor) receptor, c-Met, is a receptor tyrosine kinase that regulates cell proliferation, morphogenesis, and motility. The c-Met gene is translated into a 170 kD protein that is processed into a cell surface receptor composed of a 140 kD β transmembrane subunit and 50 kD glycosylated extra cellular α subunit.

Mutations in c-Met, over-expression of c-Met and/or HGF/SF, expression of c-Met and HGF/SF by the same cell, and over-expression and/or aberrant c-Met signalling is present in a variety of human solid tumours and is believed to participate in angiogenesis, tumour development, invasion, and metastasis. Cell lines with uncontrolled c-Met activation, for example, are both highly invasive and metastatic. A notable difference between normal and transformed cells expressing c-Met receptor is that phosphorylation of the tyrosine kinase domain in tumour cells is often independent of the presence of ligand.

C-Met mutations/alterations have been identified in a number of human diseases, including tumours and cancers—for instance, hereditary and sporadic human papillary renal carcinomas, breast cancer, colorectal cancer optionally with liver metastases, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—and leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocycticleukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma).

Over-expression of c-Met is also believed to be a potentially useful predictor for the prognosis of certain diseases, such as, for example, breast cancer, non-small cell lung carcinoma, pancreatic endocrine neoplasms, prostate cancer, oesophageal adenocarcinoma, colorectal cancer, salivary gland carcinoma, diffuse large B-cell lymphoma and endometrial carcinoma.

Because of the role of aberrant HGF/SF-Met signalling in the pathogenesis of various human cancers, inhibitors of c-Met receptor tyrosine kinase, including compound (I), have broad applications in the treatment of cancers in which Met activity contributes to the invasive/metastatic phenotype, including those in which c-Met is not over-expressed or otherwise altered. Inhibitors of c-Met also inhibit angiogenesis and therefore are believed to have utility in the treatment of diseases associated with the formation of new vasculature, such as rheumatoid arthritis and retinopathy (Michieli et al. P. 2004. Cancer Cell 6(1): 61-73).

PCT/US2006/048241 (WO 2007/075567) disclosed a method for preparing compound (I), wherein in the last step 2,2-difluoro-2-quinolin-6-ylacetohydrazide and 3-chloro-6-(1-methyl-1H-pyrazol-4-yl)pyridazine were refluxed in 1-butanol for extended periods of time to afford compound (I) (Albright, J. D., et al. 1981. J. Med. Chem. 24: 592-600) However, these relatively harsh reaction conditions could lead to formation of side products, in particular butyl difluoro (quinolin-6-yl)acetate and 3-butoxy-6-(1-methyl-1H-pyrazol-4-yl)pyridazine. Hence, subsequent to the reaction, compound (I) needed to be purified by repeated chromatography, which could reduce the yield and hamper the upscalability of the above preparation method.

Accordingly, there exists a need to provide improved methods for preparing compound (I), in particular methods which may allow for improved yield, higher purity, less manipulation and/or better upscalability of the production process.

Crystalline polymorphs and hydrates represent different solid state molecular forms of the same compound. Different crystalline polymorphs and hydrates display different crystal structures due to different packing of the molecules in the lattice. This results in different crystal symmetry and/or unit cell parameters, which directly influence the physical properties.

Crystalline polymorphic forms and hydrates are of interest to the pharmaceutical industry and especially to those involved in the development of suitable dosage forms. If the polymorphic form or hydrate is not held constant during clinical or stability studies, the exact dosage form used or studied may not be comparable from one lot to another. It is also desirable to have processes for producing a compound with the selected polymorphic form or hydrate in high purity when the compound is used in clinical studies or commercial products since impurities present may produce undesired toxicological effects. Certain polymorphic forms or hydrates may exhibit enhanced thermodynamic stability, enhanced chemical stability or may be more readily manufactured in high purity in large quantities, and thus are more suitable for inclusion in pharmaceutical formulations. Certain polymorphs or hydrates may display other advantageous physical properties such as lack of hygroscopic tendencies, improved solubility, enhanced rates of dissolution due to different lattice energies, and improved (oral) bioavailability, etc.

Accordingly, there exists a need to obtain discrete and characterised polymorphic forms and hydrates of compound (I), especially wherein such forms may entail improved properties.

Salts also represent different molecular forms of a compound. Certain salt forms may exhibit enhanced thermodynamic stability or may be more readily manufactured in high purity in large quantities, and thus are more suitable for inclusion in pharmaceutical formulations. Certain salts may display other advantageous physical properties such as lack of hygroscopic tendencies, improved solubility, enhanced rates of dissolution due to different lattice energies, and improved (oral) bioavailability, etc.

Hence, there exists a need to obtain further salt forms of compound (I), especially wherein such forms may entail improved properties.

SUMMARY OF THE INVENTION

The present invention addresses the above discussed needs in the art.

More specifically, it has surprisingly been found that compound (I) can exist in more than one polymorphic or hydrate crystalline form. These forms may be used in formulated products for the treatment of c-Met-related disorders, such as, e.g., proliferative indications including cancer. Each form may have advantage over others in, e.g., bioavailability, stability, or manufacturability. Crystalline polymorphic forms of compound (I) have been discovered which are likely to be more suitable for bulk preparation and handling than other polymorphic forms. Processes for producing these polymorphic or hydrate forms in high purity are described herein.

A further object of the present invention is to provide a process for the preparation of each polymorphic or hydrate form of compound (I), substantially free from other polymorphic or hydrate forms of compound (I).

Additionally, it is an object of the present invention to provide pharmaceutical formulations comprising compound (I) in different polymorphic or hydrate forms as discussed above, and methods of treating c-Met-related hyperproliferative conditions by administering such pharmaceutical formulations.

Accordingly, in aspects the invention provides crystalline forms and hydrates of the compound of formula (I), i.e., 6-{difluoro[6-(1-methyl-1H-pyrazol-4-yl)[1,2,4]triazolo[4,3-b]pyridazin-3-yl]methyl}quinoline:

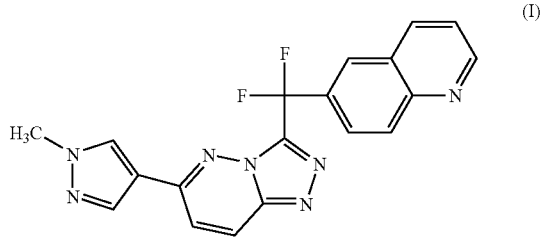 [SMILES: Cn1cc(-c2ccc3nnc(C(F)(F)c4ccc5ncccc5c4)n3n2)cn1]

(I)

Accordingly, in an aspect, the invention provides a crystalline form of the compound of formula (I) wherein the crystalline form is a substantially pure polymorph of Form I. Form I may be particularly advantageous due to its non-hygroscopic character, and good crystallographic and chemical stability.

In another aspect, the invention thus provides a crystalline form of the compound of formula (I), wherein the crystalline form has a X-ray powder diffraction (XRPD) pattern comprising peaks at diffraction angles (2θ) of 6.1±0.2, 16.5±0.2, and 19.0±0.2. Intensity variations may occur due to processes which influence intensities most importantly the processing history of the sample.

In a further aspect, the invention provides a crystalline form of the compound of formula (I), wherein the crystalline form has a XRPD pattern comprising peaks at diffraction angles (2θ) essentially the same as shown in FIG. 1.

In a further aspect, the invention thus provides a crystalline form of the compound of formula (I), wherein the crystalline form has an IR spectrum comprising peaks at absorption bands (cm$^{-1}$) of 1027±2, 835±2 and 822±2; more particularly, comprising peaks at absorption bands (cm$^{-1}$) of 1578±2, 1027±2, 982±2, 971±2, 892±2, 852±2, 835±2 and 822±2; even more particularly, comprising peaks at absorption bands (cm$^{-1}$) of 1578±2, 1027±2, 1077±2, 1050±2, 982±2, 971±2, 961±2, 932±2, 892±2, 852±2, 835±2, 822±2, 772±2, 675±2, 576±2, 554±2, and 528±2.

Also particularly, the invention provides a crystalline form of the compound of formula (I), wherein the crystalline form has an IR spectrum comprising peaks at absorption bands (cm$^{-1}$) essentially the same as shown in Table 2 or FIG. 2.

In an aspect, the polymorph Form I of compound (I) is characterised by IR spectrum peaks specific thereto, comprising peaks at absorption bands (cm$^{-1}$) of 1027±2, 982±2 and 892±2; more particularly, comprising peaks at absorption bands (cm$^{-1}$) of 1542±2, 1323±2, 1175±2, 1121±2, 1027±2, 982±2, 971±2, 961±2, 892±2, 716±2, 675±2, and 554±2.

In a further aspect, the invention thus provides a crystalline form of the compound of formula (I), wherein the crystalline form has a melting endotherm at between 199.0° C. and 203.5° C. as measured by differential scanning calorimetry (DSC) when scanning at a scan rate of 10° C. per minute.

In an aspect, the invention provides a crystalline form of the compound of formula (I) wherein the crystalline form is a substantially pure polymorph of Form II.

In yet a further aspect, the invention thus provides a crystalline form of the compound of formula (I), wherein the crystalline form has a melting endotherm at between 189.0° C. and 197.0° C., as measured by DSC when scanning at a scan rate of 10° C. per minute.

In an aspect, the invention provides a crystalline form of the compound of formula (I) wherein the crystalline form is a substantially pure polymorph of Form III.

In another aspect, the invention thus provides a crystalline form of the compound of formula (I), wherein the crystalline form has a X-ray powder diffraction (XRPD) pattern comprising peaks at diffraction angles (2θ) of 6.7±0.2, 11.3±0.2, and 15.3±0.2. Intensity variations can occur due to processes which influence intensities most importantly the processing history of the sample.

In a further aspect, the invention provides a crystalline form of the compound of formula (I), wherein the crystalline form has a XRPD pattern comprising peaks at diffraction angles (2θ) essentially the same as shown in FIG. 3.

In a further aspect, the invention thus provides a crystalline form of the compound of formula (I), wherein the crystalline form has an IR spectrum comprising peaks at absorption bands (cm$^{-1}$) of 1576±2, 1225±2, 836±2 and 830±2; more particularly, comprising peaks at absorption bands (cm$^{-1}$) of 1576±2, 1225±2, 1179±2, 1146±2, 1105±2, 1042±2, 987±2, 969±2, 836±2, 830±2 and 811±2; even more particularly, comprising peaks at absorption bands (cm⁻¹) of 1576±2, 1332±2, 1248±2, 1225±2, 1179±2, 1158±2, 1146±2, 1105±2, 1042±2, 987±2, 969±2, 932±2, 850±2, 836±2, 830±2, 811±2 and 772±2.

Also particularly, the invention provides a crystalline form of the compound of formula (I), wherein the crystalline form has a IR spectrum comprising peaks at absorption bands (cm⁻¹) essentially the same as shown in Table 4 or FIG. 4.

In an aspect, the polymorph Form III of compound (I) is characterised by IR spectrum peaks specific thereto, comprising peaks at absorption bands (cm⁻¹) of 1042±2, 987±2 and 969±2; more particularly, comprising peaks at absorption bands (cm⁻¹) of 2953±2, 1537±2, 1332±2, 1179±2, 1105±2, 1042±2, 987±2, 969±2, 714±2 and 672±2.

In an aspect, the invention provides a hydrate form of the compound of formula (I). The hydrate form may be particularly stable and therefore advantageous in aqueous media, such as for example in an aqueous suspension.

In another aspect, the invention thus provides a hydrate form of the compound of formula (I), wherein the hydrate form has a X-ray powder diffraction (XRPD) pattern comprising peaks at diffraction angles (2θ) of 8.4±0.3, 19.5±0.3, and 29.0±0.3; Intensity variations can occur due to processes which influence intensities most importantly the processing history of the sample.

In a further aspect, the invention provides a hydrate form of the compound of formula (I), wherein the hydrate form has a XRPD pattern comprising peaks at diffraction angles (2θ) essentially the same as shown in FIG. 5.

In a further aspect, the invention thus provides a hydrate form of the compound of formula (I), wherein the hydrate form has an IR spectrum comprising peaks at absorption bands (cm⁻¹) of 836±2, 825±2 and 668±2; more particularly, comprising peaks at absorption bands (cm⁻¹) of 3299±2, 1577±2, 985±2, 836±2, 825±2, 774±2, 685±2 and 668±2; even more particularly, comprising peaks at absorption bands (cm⁻¹) of 3299±2, 1577±2, 1224±2, 1183±2, 1158±2, 1114±2, 1051±2, 985±2, 836±2, 825±2, 774±2, 734±2, 716±2, 685±2, 668±2 and 481±2.

Also particularly, the invention provides a hydrate form of the compound of formula (I), wherein the hydrate form has a IR spectrum comprising peaks at absorption bands (cm⁻¹) essentially the same as shown in Table 6 or FIG. 6.

In an aspect, the hydrate form of compound (I) is characterised by IR spectrum peaks specific thereto, comprising peaks at absorption bands (cm⁻¹) of 3299±2, 985±2 and 668±2; more particularly, comprising peaks at absorption bands (cm⁻¹) of 3299±2, 1539±2, 1481±2, 1341±2, 1183±2, 1126±2, 1114±2, 991±2, 985±2, 977±2, 914±2 and 668±2.

In a related aspect, the invention provides a solid form of the compound of formula (I) comprising at least 50%, e.g., at least 60%, preferably at least 70%, e.g., at least 80%, more preferably at least 90%, e.g. at least 95% or at least 98% by weight of polymorph Form I.

In an aspect, the invention provides a solid form of the compound of formula (I) comprising at least 50%, e.g., at least 60%, preferably at least 70%, e.g., at least 80%, more preferably at least 90%, e.g. at least 95% or at least 98% by weight of polymorph Form III.

In an aspect, the invention provides a solid form of the compound of formula (I) comprising at least 50%, e.g., at least 60%, preferably at least 70%, e.g., at least 80%, more preferably at least 90%, e.g. at least 95% or at least 98% by weight of the above hydrate form.

In an aspect, the invention provides a solid form of the compound of formula (I) comprising a mixture of at least two forms selected from polymorph Forms I, II and III and the hydrate form. Preferably, said mixture may constitute at least 50%, e.g., at least 60%, preferably at least 70%, e.g., at least 80%, more preferably at least 90%, e.g., at least 95% or even 100% by weight of the solid form of the compound of formula (I).

In a preferred embodiment, the solid form of the compound of formula (I) can comprise a mixture of polymorph Form I and polymorph Form III. Said mixture of polymorph Forms I and III may preferably contain (w/w): about 90% polymorph Form I and about 10% polymorph Form III; or about 80% polymorph Form I and about 20% polymorph Form III; or about 70% polymorph Form I and about 30% polymorph Form III; or about 60% polymorph Form I and about 40% polymorph Form III.

In a further aspect, the invention provides methods for preparing the above polymorphic forms and hydrate of compound (I), in particular the polymorphic Forms I and III and the hydrate form.

In another aspect, the invention provides a process for preparing the compound of formula (I): comprising:
(a) reacting an intermediate of formula (II)

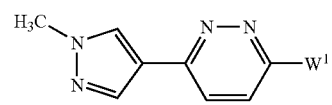

(II)

wherein W¹ is a leaving group, with an intermediate of formula (III)

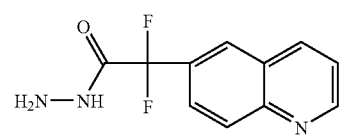

(III)

in the presence of an acid, thereby obtaining a salt of the compound of formula (I); and
(b) contacting said salt with a base, thereby obtaining the compound of formula (I).

Preferably, the acid employed in the above step (a) has pKa less than about 3, more preferably equal or less than 1. In particularly preferred embodiments, the acid employed in the step (a) may be a hydrohalic acid, more preferably HCl or HBr, sulphuric acid ($H_2SO_4$), trifluoroacetic acid, or a sulphonic acid, more preferably p-toluene sulphonic acid, p-bromobenzene sulphonic acid, trifluoromethane sulphonic acid, camphor sulphonic acid, methane sulphonic acid or ethane sulphonic acid.

The inventors surprisingly realised that inclusion of an acid in the reaction of intermediates (II) and (III) greatly facilitates said reaction. Consequently, the reaction may take place at temperatures considerably lower than previously (e.g., at less than 120° C., for example between 80° C. and 110° C.), which reduces the formation of side products. Therefore, column chromatography can be avoided to obtain pure compound (I). In addition, inclusion of the acid may also shorten the reaction time, preferably to less than 20 hours, more preferably to less than 15 hours, even more preferably to 10 hours or less, such a, e.g., to between about 4 hours and about 10 hours. This can also reduce the chance of side-product formation, as well as expedites the process. Moreover, the yield of the reaction can so be improved to as much as about 85% or more conversion in reaction mixture, and as much as about 75% or more, or about 80% or more of isolated yield. Also, due to the possibility to precipitate the formed salt from the reaction mixture, the isolation of the salt from reaction mixture as a pure compound is greatly simplified, thereby avoiding extensive work-up and extraction procedures.

Accordingly, the invention also provides salts of the compound of formula (I), more preferably salts with acids having pKa equal or lower than 1, and even more preferably salts with HCl, HBr, methane sulphonic acid, ethane sulphonic acid, or p-toluene sulphonic acid. As explained above, such salts are particularly useful intermediates in the preparation of the compound of formula (I). In addition, as can be appreciated, such salts also represent additional forms of the compound (I) which may display distinct pharmacological advantages, such as, e.g., improved stability, solubility, bioavailability, etc. In particular, the invention provides a salt of the compound of formula (I) with an acid provide that the acid is not HCl, more preferably salts with acids having pKa equal or lower than 1, and even more preferably salts with HBr, methane sulphonic acid, ethane sulphonic acid, or p-toluene sulphonic acid.

In view hereof, the invention also provides a process for preparing a salt of the compound of formula (I), comprising reacting the intermediate (II) with the intermediate (III) in the presence of an acid.

In related aspect, the invention provides any of the following:
pharmaceutical compositions comprising a crystalline form of the compound of formula (I), wherein the crystalline form is a substantially pure polymorph of Form I;
pharmaceutical compositions comprising a crystalline form of the compound of formula (I), wherein the crystalline form is a substantially pure polymorph of Form III;
pharmaceutical compositions comprising a crystalline form of the compound of formula (I), wherein the crystalline form is a substantially pure hydrate as taught herein;
pharmaceutical compositions comprising a solid form of the compound of formula (I), wherein said solid form comprises a mixture of at least two forms selected from polymorph Forms I, II and III and the hydrate form; preferably, said mixture may constitute at least 50%, e.g., at least 60%, preferably at least 70%, e.g., at least 80%, more preferably at least 90%, e.g., at least 95% or even 100% by weight of said solid form;
pharmaceutical compositions comprising a solid form of the compound of formula (I), wherein said solid form comprises a mixture of polymorph Form I and Form III; preferably, said mixture may contain (w/w): about 90% polymorph Form I and about 10% polymorph Form III; or about 80% polymorph Form I and about 20% polymorph Form III; or about 70% polymorph Form I and about 30% polymorph Form III; or about 60% polymorph Form I and about 40% polymorph Form III; or
pharmaceutical compositions comprising a salt of the compound of formula (I); preferably, said salt may be with an acid having pKa equal or lower than 1; more preferably, said salt may be with an acid chosen from: HCl, HBr, methane sulphonic acid, ethane sulphonic acid, or p-toluene sulphonic acid, more preferably with any of HBr, methane sulphonic acid, ethane sulphonic acid, or p-toluene sulphonic acid.

In a further aspect, the invention provides any of the polymorph Form I, II or III of compound of formula (I) or any mixture thereof; and/or the hydrate form of the compound of formula (I); and/or a salt of the compound of formula (I); as protein tyrosine kinase modulators, particularly inhibitors of c-Met, and particularly for reducing or inhibiting kinase activity of c-Met in a cell or a subject, and/or for modulating c-Met expression in a cell or subject, and/or for preventing or treating, preferably treating, in a subject a cell proliferative disease and/or a disorder related to c-Met.

In another aspect, the invention provides use of any of the polymorph Form I, II or III of compound of formula (I) or any mixture thereof; and/or the hydrate form of the compound of formula (I); and/or a salt of the compound of formula (I); for the manufacture of a medicament for reducing or inhibiting kinase activity of c-Met in a subject, and/or for modulating c-Met expression in a subject, and/or for preventing or treating, preferably treating, in a subject a cell proliferative disease and/or a disorder related to c-Met.

In a related aspect, the invention provides the use of any of the polymorph Form I, II or III of compound of formula (I) or any mixture thereof; and/or the hydrate form of the compound of formula (I); and/or a salt of the compound of formula (I); for reducing or inhibiting kinase activity of c-Met in a cell in vitro, and/or modulating c-Met expression in a cell in vitro.

Also, the invention provides methods for reducing or inhibiting kinase activity of c-Met in a subject and/or for modulating c-Met expression in a cell or subject, and/or for preventing or treating, preferably treating, in a subject a cell proliferative disease and/or a disorder related to c-Met, comprising administering to said subject a therapeutically effective amount of any of the polymorph Form I, II or III of compound of formula (I) or any mixture thereof; and/or the hydrate form of the compound of formula (I); and/or a salt of the compound of formula (I). Preferably, these can be administered in the form of a pharmaceutical composition as taught herein. Preferably, the subject may be an animal, more preferably warm-blooded animal, yet more preferably mammal, e.g., human or non-human mammal.

These and further aspects and preferred embodiments of the invention are described in the following sections and in the appended claims.

DETAILED DESCRIPTION OF THE INVENTION

Figure 1:
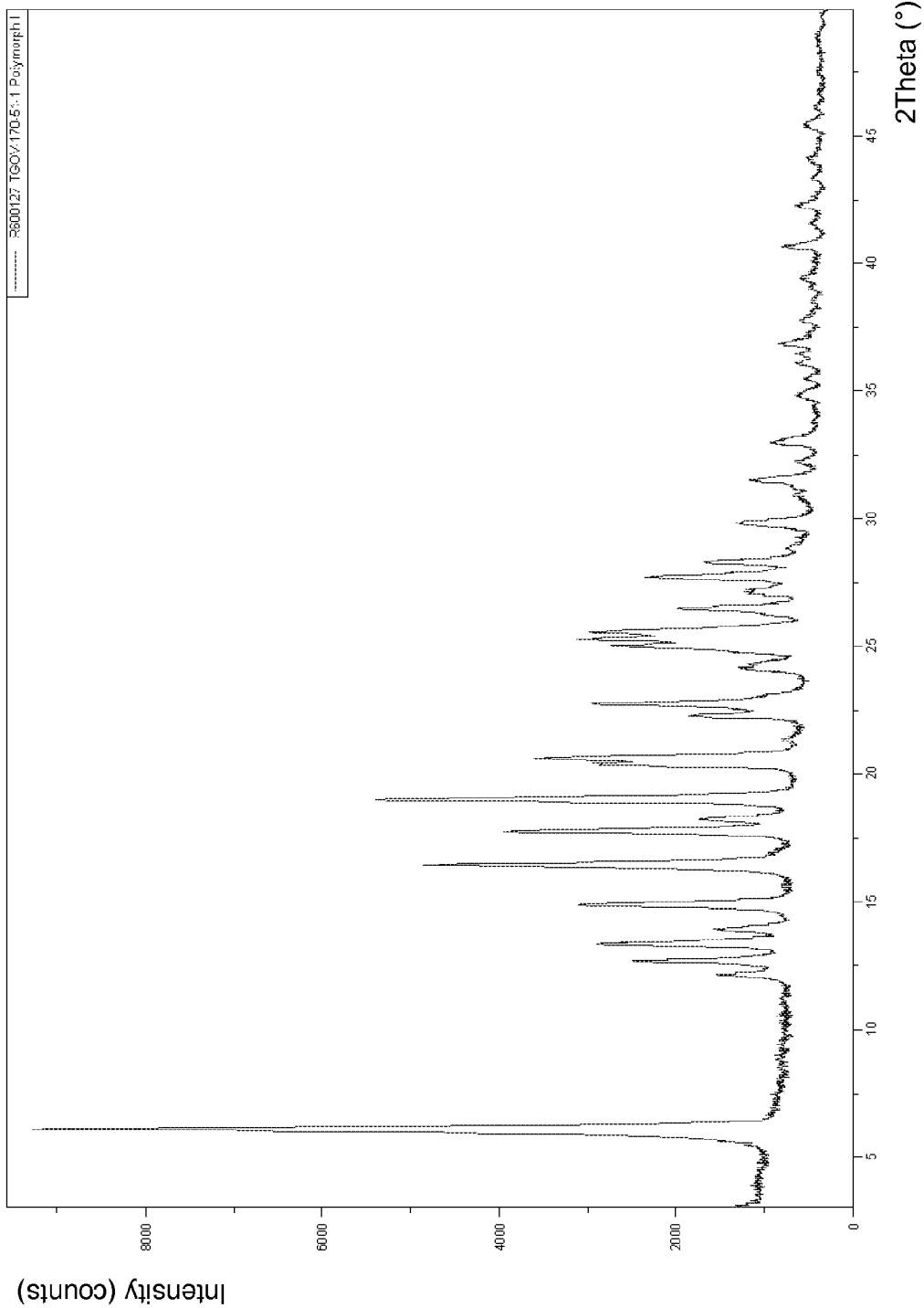
FIG. 1 illustrates XRPD pattern for polymorph Form I of compound of formula (I).

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The discussion of the background to the invention herein is included to explain the context of the present invention. This is not to be taken as an admission that any of the material referred to was published, known, or part of the common general knowledge in any country as of the priority date of any of the claims.

Abbreviations

As used herein, the following abbreviations are intended to have the following meanings (additional abbreviations are provided where needed throughout the specification):
BTEAC Benzyltriethylammonium chloride
DAST dialkylaminosulphur trifluoride
Deoxo-Fluor™ bis(2-methoxyethyl)aminosulphur trifluoride
DIPEA N,N'-diisopropylethylamine
DMSO dimethyl sulfoxide
DSC differential scanning calorimetry
ICH International Conference on Harmonization
iPr isopropyl
IR infrared
OAc acetate
OMs methanesulphonyloxy (—OSO$_2$CH$_3$)
OTf triflate group (—OSO$_2$CF$_3$)
OTs p-toluenesulphonyloxy (—OSO$_2$C$_6$H$_5$CH$_3$)
Pd/C palladium/carbon black
PdCl$_2$(PPh$_3$)$_2$ dichlorobis (triphenylphosphine)palladium (II)
Pd(dppf)Cl$_2$ dichloro[1,1'-bis(diphenylphosphino) ferrocene] palladium (II)
Pd(OAc)$_2$ palladium acetate
Pd(PPh$_3$)$_4$ tetrakis(triphenylphosphine)palladium (0)
Peppsi-iPr pyridine-enhanced pre-catalyst preparation stabilization and initiation (trademark of Sigma-Aldrich)
RT room temperature
TGA thermal gravimetric analysis
THF tetrahydrofuran
XRPD X-ray powder diffraction Polymorphic Forms of the Compound of Formula (I)

The term "polymorph" refers to a crystalline form of a compound with a distinct spatial lattice arrangement as compared to other crystalline forms of the same compound.

The term "hydrate" refers to a solid state molecular form of a compound comprising bound water in the crystalline structure.

The term "slurry" refers to a solid substance suspended in a liquid medium, typically water or an organic solvent.

The invention provides several polymorph and hydrate crystalline forms, and salts, of the compound of formula (I). Each crystalline form of said compound can be characterised by one or more of the following: XRPD pattern (i.e., X-ray powder diffraction peaks at various diffraction angles (2θ)); melting point onset (and onset of dehydration for hydrated forms) as illustrated by endotherms of a DSC thermogram; re-crystallisation onset illustrated by a DSC thermogram; IR spectrometry; TGA behaviour; adsorption of moisture; aqueous solubility; light stability under ICH high intensity light conditions, and physical and chemical storage stability.

The term "X-ray powder diffraction pattern" refers to the experimentally observed diffractogram or parameters derived there from. X-ray powder diffraction patterns are characterised by peak positions (abscissa) and display peak intensities (ordinate).

The term "peak intensities" refers to measured (counts) or relative signal intensities within a given X-ray diffraction pattern. Factors which can affect the relative peak intensities are sample thickness and preferred orientation (i.e., the crystalline particles are not distributed randomly). The term "peak positions" as used herein refers to X-ray reflection positions as measured and observed in X-ray powder diffraction experiments. Peak positions are directly related to the dimensions of the unit cell. The peaks, identified by their respective peak positions, have been extracted from the diffraction patterns for the various polymorphic Forms I or III or the hydrate of compound of formula (I).

The term "relative intensity" refers to an intensity value derived from a sample X-ray diffraction pattern or an IR spectrum. The complete ordinate range scale for a diffraction pattern is assigned a value of 100.

The term "2 theta value" or "2θ" refers to the peak position based on the experimental setup of an XRD experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ).

The XRPD pattern for each polymorph form, hydrate or salt of compound (I) was measured on a Philips X'PertPRO MPD diffractometer PW3050/60 with generator PW3040. The instrument is equipped with a Cu LFF X-ray tube PW3373/00. The compound was spread on a zero background sample holder. The instrument parameters were— measurement conditions were as follows—generator voltage 45 kV; generator amperage 40 mA; geometry Bragg-Brentano; stage: spinner stage. The measurement conditions were as follows—scan mode: continuous; scan range: 3 to 50° 2θ; step size: 0.0167°/step; counting time: 29.845 sec/step; spinner revolution time: 1 sec; radiation type: CuKα; radiation wavelength: 1.54056 Å; incident beam path (program. divergence slit: 15 mm; Soller slit: 0.04 rad; beam mask: 15 mm; anti scatter slit: 1°; beam knife: +); diffracted beam path (long anti scatter shield: +; Soller slit: 0.04 rad; Ni filter: +; detector: X'Celerator.

One of skill in the art will appreciate that the peak positions (2θ) may show some inter-apparatus variability, typically as much as +0.1° or −0.1°. Accordingly, where peak positions (2θ) are reported, one of skill in the art will recognise that such numbers are intended to encompass such inter-apparatus variability. Furthermore, where the solid forms of the present invention are described as having a XRPD pattern essentially the same as that shown in a given figure, the term "essentially the same" is intended to encompass such inter-apparatus variability in diffraction peak positions. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

The IR spectrum for each polymorphic form or hydrate of compound (I) was measured using a Thermo Nexus 670 FTIR spectrophotometer with a DTGS detector with KBr windows and a Ge on KBr beamsplitter. The system was equipped with a Harrick Split Pea micro ATR accessory with Si crystal. Spectra were collected using the following parameters— number of scans: 32; resolution: 1 cm$^{-1}$; wavelength range: 4000 to 400 cm$^{-1}$. All spectra were normalized and baseline corrected.

Different polymorphic or hydrate forms or salts of compound (I) were also distinguished using differential scanning calorimetry (DSC). DSC measures the difference in heat energy between a solid sample and an appropriate reference with an increase in temperature. DSC thermograms are characterised by endotherms (indicating energy uptake) and also by exotherms (indicating energy release), typically as the sample is heated. The DSC thermographs were obtained using a TA-Instruments Q1000 MTDSC equipped with a RCS cooling unit. Samples were weighed (about 3 mg) into standard aluminium TA-Instrument sample pan closed with an appropriate cover. Following parameters were used—initial temperature: 25° C.; heating rate: 10° C./min; final temperature: 300° C.; nitrogen flow: 50 ml/min. Depending upon the rate of heating (i.e., the scan rate) at which the DSC analysis is conducted, the way the DSC onset temperature is defined and determined, the calibration standard used, the instrument calibration, and the relative humidity and chemical purity of the sample, the endotherms exhibited by the compounds of the invention may vary (by about 0.01-5° C., for crystal polymorph melting and by about 0.01-20° C. for hydrate dehydration above or below the endotherms. For any given example, the observed endotherms may also differ from instrument to instrument; however, it will generally be within the ranges defined herein provided the instruments are calibrated similarly.

Different polymorphic or hydrate forms or salts of compound (I) were also distinguished using thermal gravimetric analysis (TGA). TGA is a testing procedure in which changes in weight of a specimen are recorded as the specimen is heated in air or in a controlled atmosphere such as nitrogen. Thermogravimetric curves (thermograms) provide information regarding solvent and water content and the thermal stability of materials. TGAs were performed on TA Instruments Q500 thermogravimeter, using the following parameters—initial temperature: room temperature; heating rate: 20° C./min; resolution factor: 4; final condition: 300° C. or <80 [(w/w) %].

Different polymorphic or hydrate forms or salts of compound (I), may also be distinguished by different stabilities and different solubilities.

The polymorph or hydrate forms of the invention may be preferably substantially pure, meaning that a given polymorph of the compound of formula (I) includes less than 10%, e.g., less than 9% or less than 8%, preferably less than 7%, e.g., less than 6%, more preferably less than 5%, e.g., less than 4%, even more preferably less than 3%, e.g., less than 2%, and still more preferably less than 1% by weight of impurities, including other polymorph or amorphous forms of the compound of formula (I). Such purity may be determined, e.g., by XRPD.

The salt of the invention may be preferably substantially pure, meaning that a given salt of the compound of formula (I) includes less than 10%, e.g., less than 9% or less than 8%, preferably less than 7%, e.g., less than 6%, more preferably less than 5%, e.g., less than 4%, even more preferably less than 3%, e.g., less than 2%, and still more preferably less than 1% by weight of impurities, including free base of the compound of formula (I).

The present solid forms may also exist together in a mixture. Mixtures of polymorph or hydrate forms or salts of the invention will have X-ray diffraction peaks characteristic of each of the forms present in the mixture. For example, a mixture of two polymorphs will have a XRPD pattern that is a convolution of the XRPD patterns corresponding to the substantially pure polymorphs.

Polymorph Form I

Polymorph Form I is an anhydrous crystal of the compound of formula (I). Form I is non-hygroscopic, and particularly crystallographically and chemically stable. Form I is believed to be the thermodynamically most stable form of currently identified polymorphs of compound (I). In addition, the free base Form I showed similar bioavailability in rat models compared to the salts of compound (I).

Figure 7:
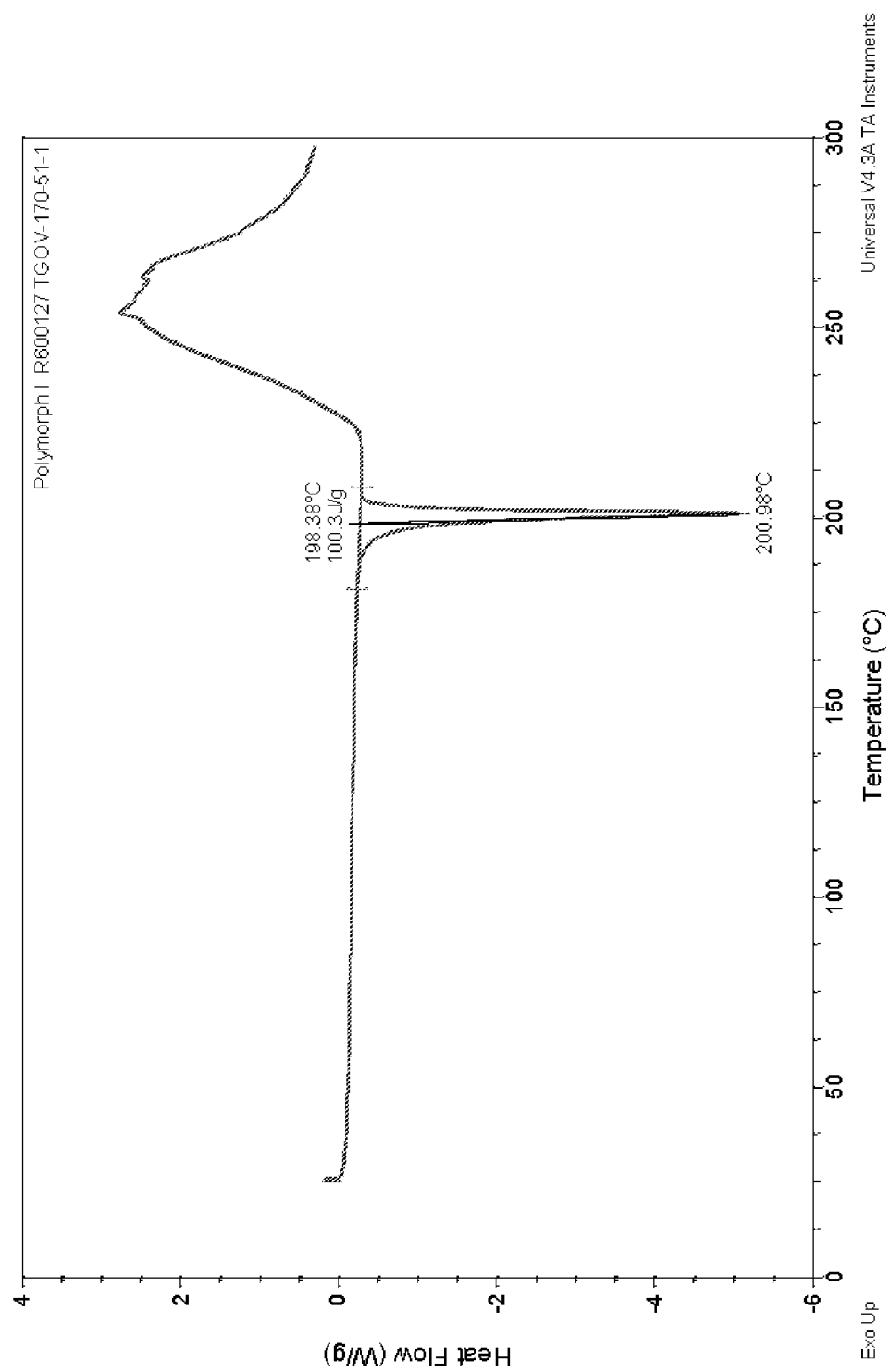
FIG. 7 illustrates DSC scan for polymorph Form I of compound of formula (I).

DSC at a scan rate of 10° C./min yields a melting endotherm for Form I typically between 199.0° C. and 203.5° C. (FIG. 7).

Form I is characterised by a XRPD pattern comprising peaks at diffraction angles (2θ) as shown in Table 1. The 2θ angles shown in Table 1 may vary by about 0.2 2θ.

TABLE 1

| Angle - 2 theta |
| --- |
| 6.1 |
| 16.5 |
| 19.0 |

FIG. 1 provides exemplary XRPD pattern for Form I.

Form I is characterised by infrared (IR) spectrum comprising peaks at absorption bands (cm$^{-1}$) as shown in Table 2. The absorption bands shown in Table 2 may vary by about 2 cm$^{-1}$.

TABLE 2

| Absorption band | Relative intensity (%) |
| --- | --- |
| 3116 | W |
| 3053 | W |
| 2989 | VW |
| 2943 | W |
| 2804 | VW |
| 1619 | W |
| 1578 | S |
| 1542 | W |
| 1497 | M |
| 1466 | M |
| 1427 | M |
| 1416 | M |
| 1381 | W |
| 1358 | W |
| 1336 | M |
| 1323 | W |
| 1302 | W |
| 1268 | M |
| 1245 | M |
| 1227 | M |
| 1175 | M |

TABLE 2-continued

| Absorption band | Relative intensity (%) |
|---|---|
| 1156 | M |
| 1121 | M |
| 1087 | M |
| 1077 | M |
| 1050 | M |
| 1027 | VS |
| 982 | S |
| 971 | S |
| 961 | M |
| 932 | M |
| 892 | S |
| 852 | S |
| 835 | VS |
| 822 | VS |
| 772 | M |
| 737 | W |
| 716 | W |
| 675 | M |
| 576 | M |
| 554 | M |
| 536 | W |
| 528 | M |
| 492 | W |
| 481 | W |
| 459 | W |

VW (very weak): 0% to 10%;
W (weak): >10% to 30%;
M (medium): >30% to 60%;
S (strong): >60% to 90%;
VS (very strong): >90% to 100%

Figure 2:
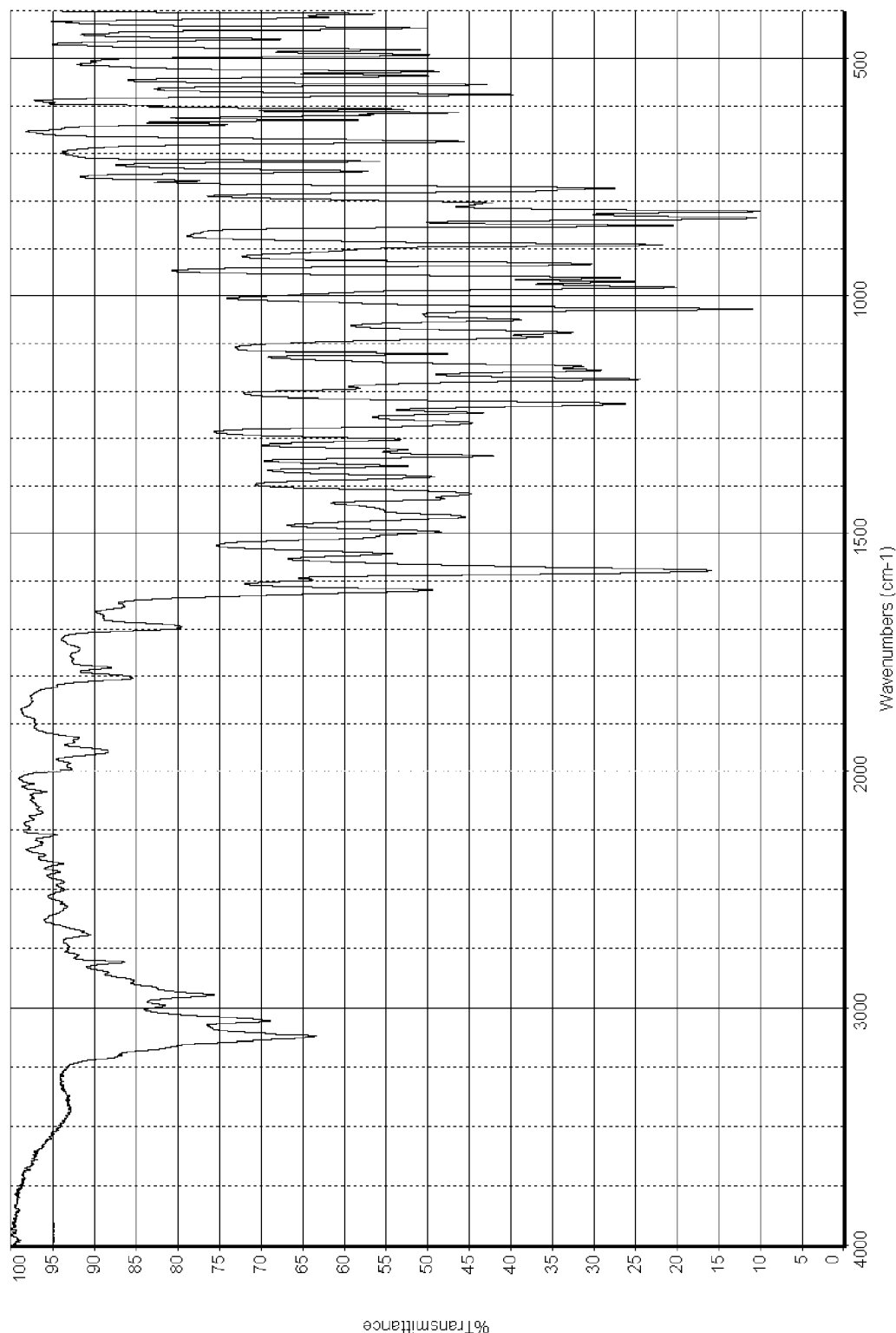
FIG. 2 illustrates IR spectrum for polymorph Form I of compound of formula (I).

FIG. 2 provides exemplary IR spectra for Form I.

The aqueous solubility of Form I at different pH is summarised in Table 7 (see Example 4).

Polymorph Form I can be prepared by crystallising the compound of formula (I) from alcohol solvents and collecting the so-formed crystals. Particularly suitable alcohol solvents include ethanol, isopropanol or higher alcohols, such as, e.g., butanol or pentanol, or mixtures thereof. The preparation may be conducted at a temperature between RT and the reflux temperature of the solvent, preferably at a temperature greater than about 50° C., e.g., greater than about 60° C., more preferably greater than about 70° C., e.g., greater than about 80° C. The preparation may proceed for a time period of at least 2 hours, preferably for at least 4 hours.

Polymorph Form I can also be prepared by crystallising the compound of formula (I) from aprotic solvents and collecting the so-formed crystals. Particularly suitable aprotic solvents include ethyl acetate or dichloromethane, or preferably mixtures thereof. The preparation may be conducted at a temperature between RT and the reflux temperature of the solvent and may proceed for a time period of at least 2 hours, preferably for at least 4 hours.

In addition, polymorph Form I can also be obtained by crystallising the compound of formula (I) from a mixture of an alcohol and water at an elevated temperature, and collecting the so-formed crystals. Particularly suitable alcohol is ethanol or methanol. The mixture may contain preferably between about 40:60 and about 90:10 alcohol:water (vol/vol), more preferably between about 50:50 and about 80:20 alcohol:water (vol/vol). The crystallisation may be effected at a temperature of at least 60° C.

Polymorph Form II

Figure 8:
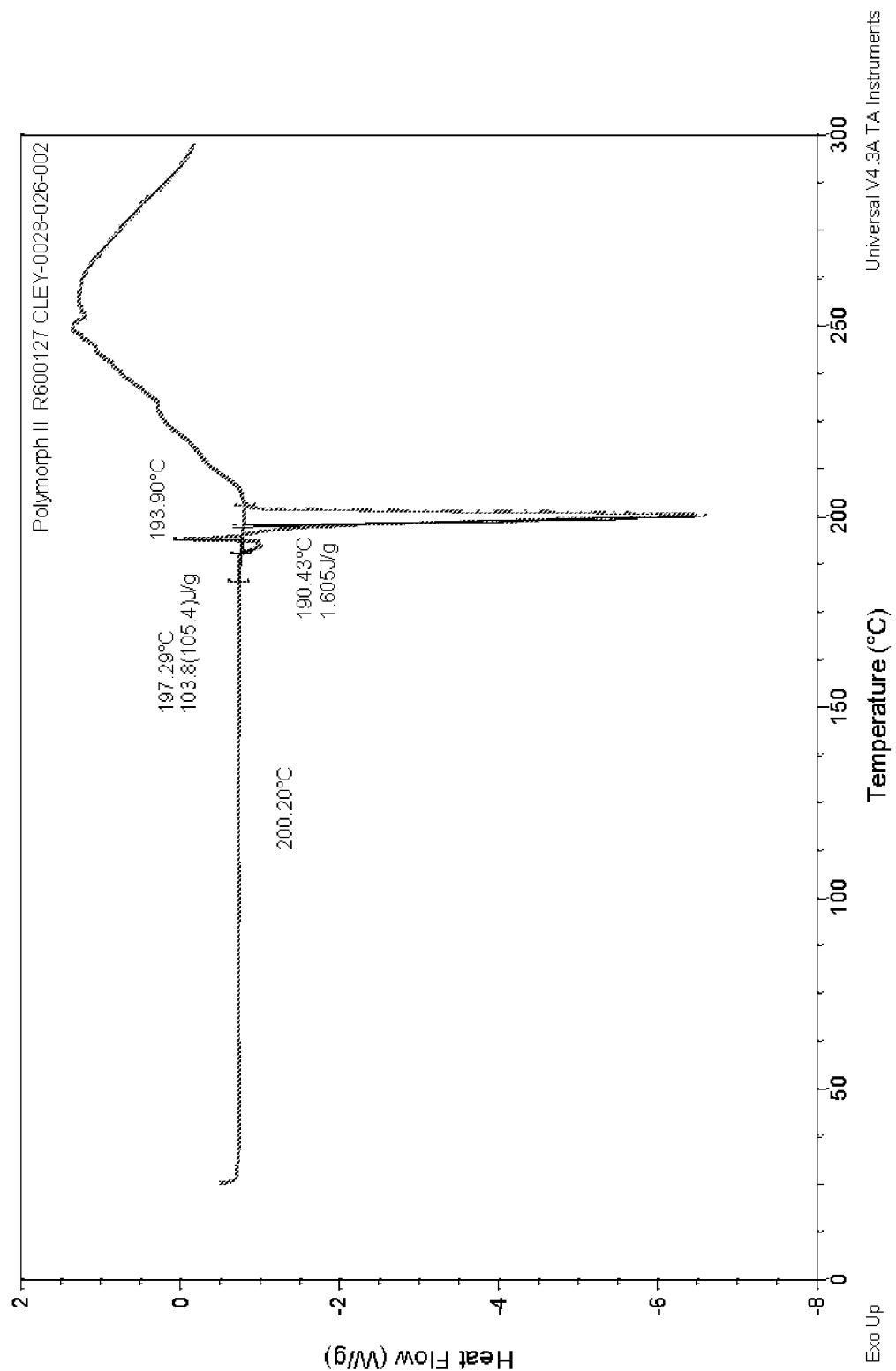
FIG. 8 illustrates DSC scan showing melting endotherm of polymorph Form II of compound of formula (I).

Polymorph Form II is observed by DSC and can be obtained by thermal treatment and re-crystallisation of Form III. DSC at a scan rate of 10° C./min may yield a melting endotherm for Form II typically between 189.0° C. and 197.0° C., (FIG. 8).

Polymorph Form III

Polymorph Form III is an anhydrous crystal of the compound of formula (I).

Figure 9:
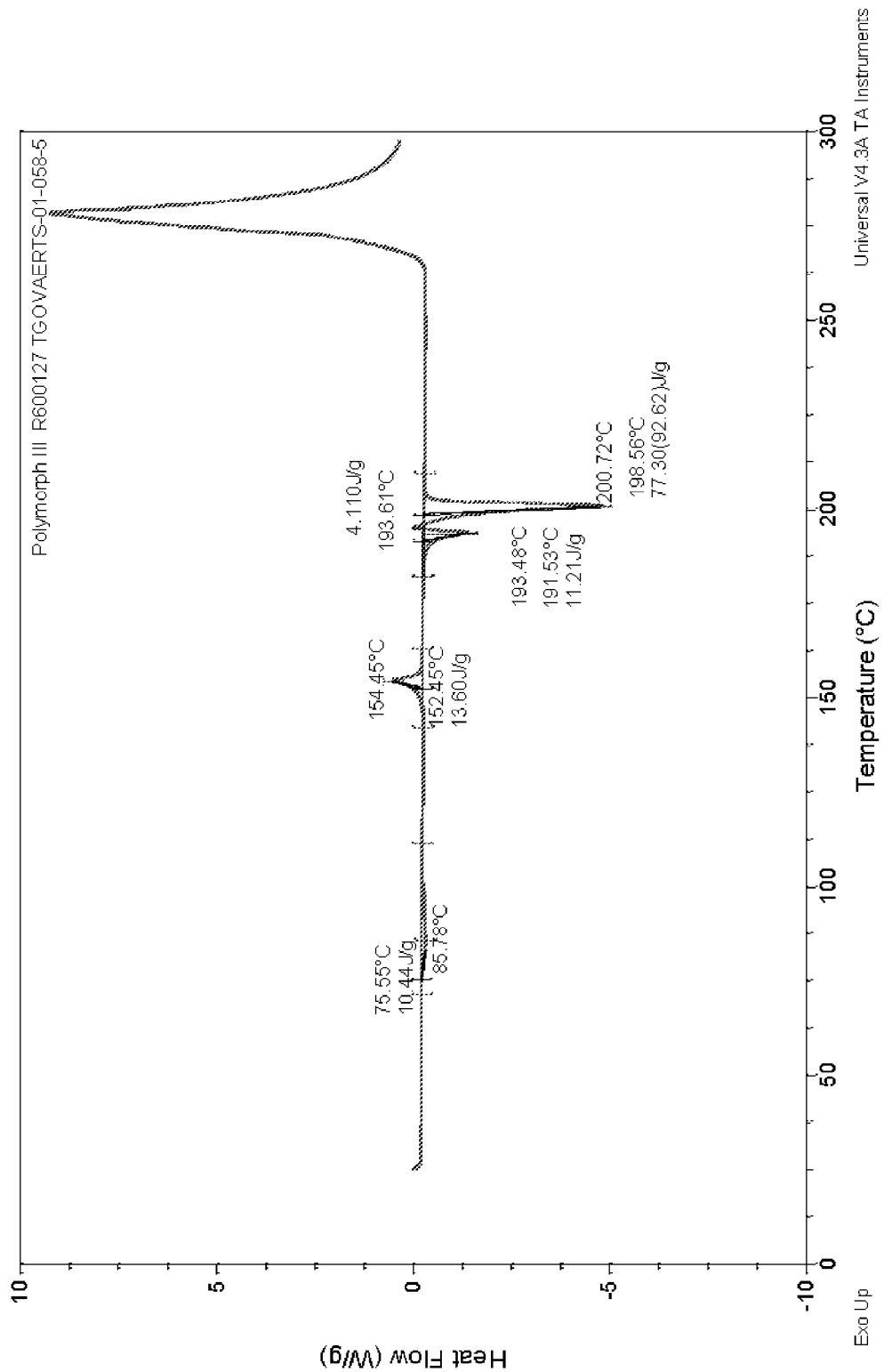
FIG. 9 illustrates DSC scan for polymorph Form III of compound of formula (I).

DSC at a scan rate of 10° C./min may yield a melting endotherm for Form III (FIG. 9; in this particular curve, signal at 193° C. it is due to Form II; the curve shows conversion of Form III).

Form III is characterised by a XRPD pattern comprising peaks at diffraction angles (2θ) as shown in Table 3. The 2θ angles shown in Table 3 may vary by about 0.2 2θ.

TABLE 3

| Angle - 2 theta |
|---|
| 6.7 |
| 11.3 |
| 15.3 |

Figure 3:
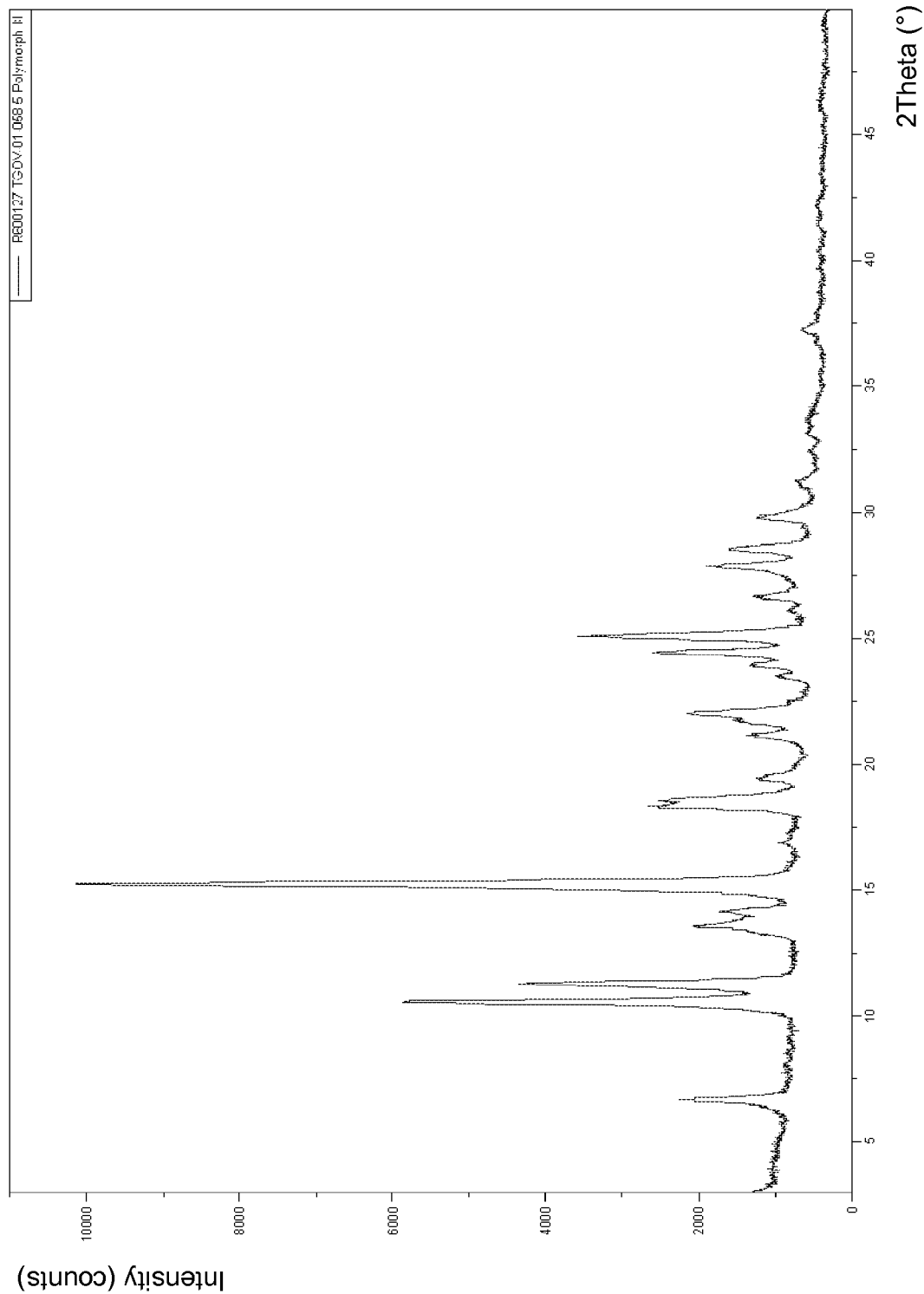
FIG. 3 illustrates XRPD pattern for polymorph Form III of compound of formula (I).

FIG. 3 provides exemplary XRPD pattern for Form III.

Form III is characterised by infrared (IR) spectrum comprising peaks at absorption bands (cm$^{-1}$) as shown in Table 4. The absorption bands shown in Table 4 may vary by about 2 cm$^{-1}$.

TABLE 4

| Absorption band | Relative intensity (%) |
|---|---|
| 3114 | W |
| 3053 | W |
| 3014 | W |
| 2953 | W |
| 1614 | W |
| 1597 | W |
| 1576 | S |
| 1538 | W |
| 1502 | W |
| 1463 | W |
| 1443 | W |
| 1414 | W |
| 1377 | W |
| 1358 | W |
| 1332 | M |
| 1302 | W |
| 1267 | W |
| 1248 | M |
| 1225 | S |
| 1179 | M |
| 1158 | M |
| 1146 | M |
| 1105 | M |
| 1078 | W |
| 1042 | M |
| 987 | M |
| 969 | M |
| 932 | M |
| 898 | W |
| 850 | M |
| 836 | VS |
| 830 | S |
| 811 | M |
| 780 | M |
| 772 | M |
| 736 | W |
| 714 | M |
| 672 | M |
| 599 | M |
| 574 | W |
| 568 | M |
| 533 | W |
| 524 | W |
| 498 | W |
| 485 | W |

TABLE 4-continued

| Absorption band | Relative intensity (%) |
| --- | --- |
| 459 | W |
| 432 | W |

VW (very weak): 0% to 10%;
W (weak): >10% to 30%;
M (medium): >30% to 60%;
S (strong): >60% to 90%;
VS (very strong): >90% to 100%

Figure 4:
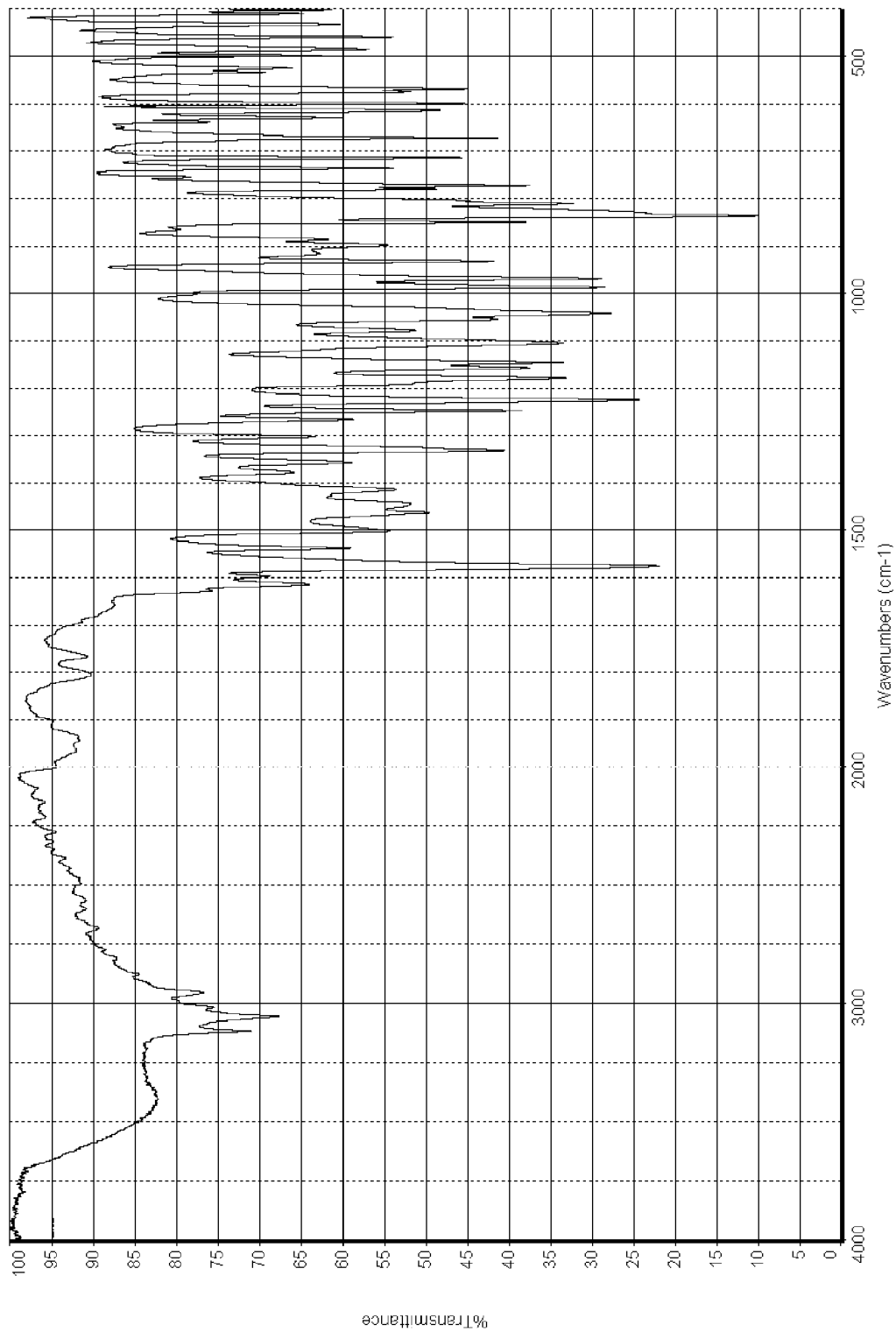
FIG. 4 illustrates IR spectrum for polymorph Form III of compound of formula (I).

FIG. 4 provides exemplary IR spectra for Form III.

The aqueous solubility of Form III at different pH is summarised in Table 7 (see Example 4).

Polymorph Form III can be prepared by neutralising a salt of the compound of formula (I) dissolved in an aqueous solvent with a base and collecting the so-formed precipitate. An exemplary salt may be the methanesulphonate (mesylate) salt of the compound of formula (I); a suitable aqueous solvent may be, for example, ethyl acetate/water mixture; an appropriate base is, e.g., ammonia.

Polymorph Form III can also be prepared by crystallising the compound of formula (I) from alcohol/water systems at a temperature between RT and about 60° C. and collecting the so-formed crystals. Particularly suitable alcohol/water mixtures include methanol/water and ethanol/water systems at between about 30:70 and about 70:30 alcohol:water (vol/vol).

Polymorph Form III can further be prepared by precipitating the compound of formula (I) from aqueous HCl at a concentration of about 0.01N and collecting the so-formed crystals.

In addition, polymorph Form III can also be obtained by thermal treatment at about 115° C. of a hydrate of the compound of formula (I).

Polymorph Form III can as well be prepared by slurrying Form I in aprotic polar solvent/water systems at a temperature of about 60° C. and collecting the so-formed crystals. Particularly suitable solvent systems are acetone/water mixtures at between about 30:70 and about 50:50 acetone:water (vol/vol).

Hydrate Form

The invention further contemplates a hydrate form of the compound of formula (I). The hydrate form is particularly stable in aqueous media, such as for example in an aqueous suspension.

The hydrate form is characterised by a XRPD pattern comprising peaks at diffraction angles (2θ) as shown in Table 5. The 2θ angles shown in Table 5 may vary by about 0.3 2θ.

TABLE 5

| Angle - 2 theta |
| --- |
| 8.4 |
| 19.5 |
| 29.0 |

Figure 5:
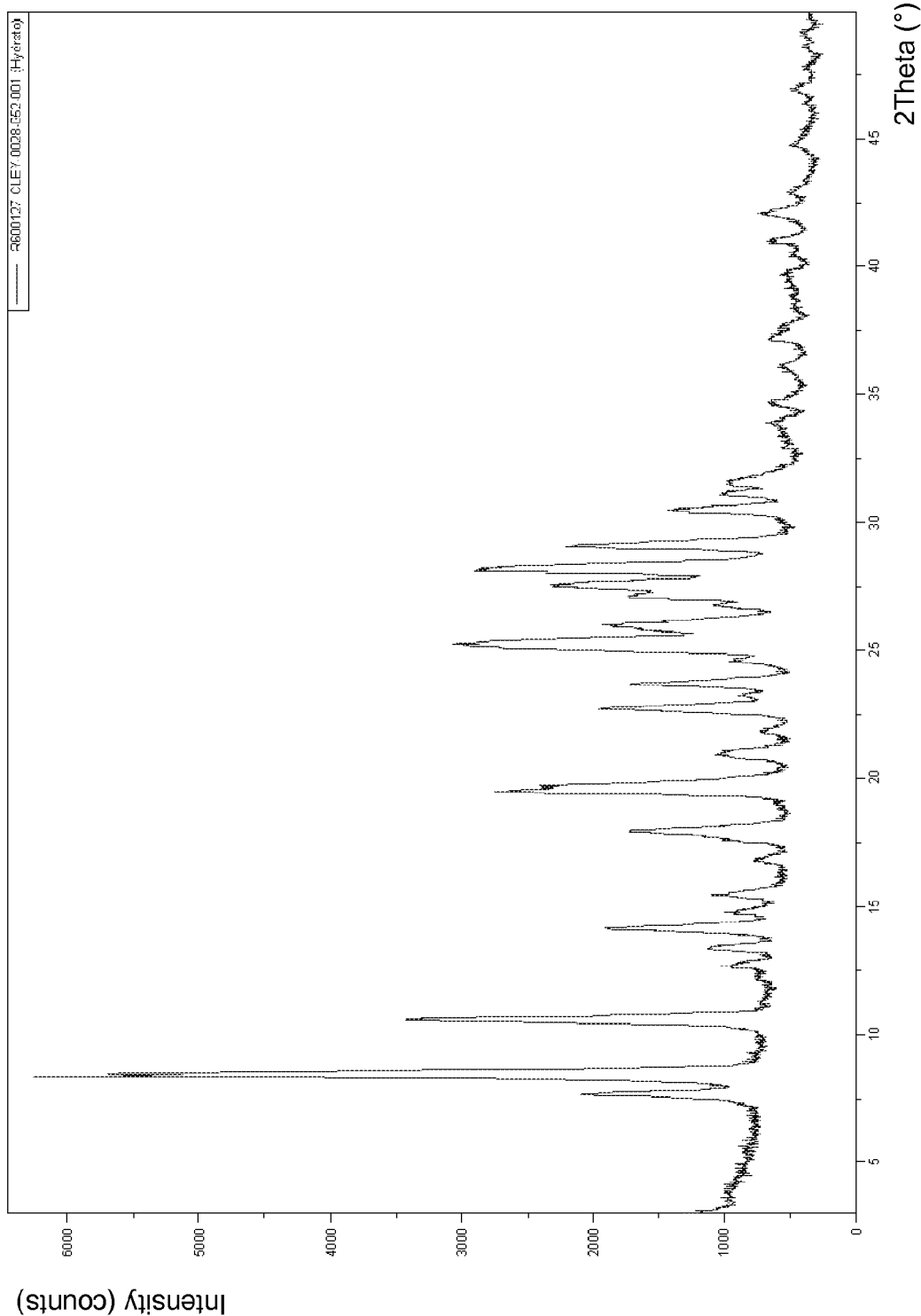
FIG. 5 illustrates XRPD pattern for hydrate of compound of formula (I).

FIG. 5 provides exemplary XRPD pattern for the hydrate form.

The hydrate form is characterised by infrared (IR) spectrum comprising peaks at absorption bands (cm$^{-1}$) as shown in Table 6. The absorption bands shown in Table 6 may vary by about 2 cm$^{-1}$.

TABLE 6

| Absorption band | Relative intensity (%) |
| --- | --- |
| 3299 | S |
| 3116 | M |
| 2954 | W |
| 1674 | W |
| 1630 | W |
| 1618 | W |
| 1598 | W |
| 1577 | S |
| 1539 | M |
| 1506 | M |
| 1481 | M |
| 1465 | M |
| 1428 | W |
| 1415 | W |
| 1356 | M |
| 1341 | M |
| 1336 | M |
| 1307 | M |
| 1275 | W |
| 1253 | M |
| 1224 | S |
| 1183 | S |
| 1158 | S |
| 1114 | S |
| 1088 | M |
| 1068 | M |
| 1051 | S |
| 1031 | W |
| 991 | M |
| 985 | S |
| 977 | M |
| 936 | M |
| 914 | M |
| 875 | W |
| 850 | M |
| 836 | VS |
| 825 | VS |
| 808 | M |
| 774 | S |
| 734 | S |
| 716 | S |
| 685 | S |
| 668 | VS |
| 498 | M |
| 481 | S |
| 458 | M |
| 432 | M |

VW (very weak): 0% to 10%;
W (weak): >10% to 30%;
M (medium): >30% to 60%;
S (strong): >60% to 90%;
VS (very strong): >90% to 100%

Figure 6:
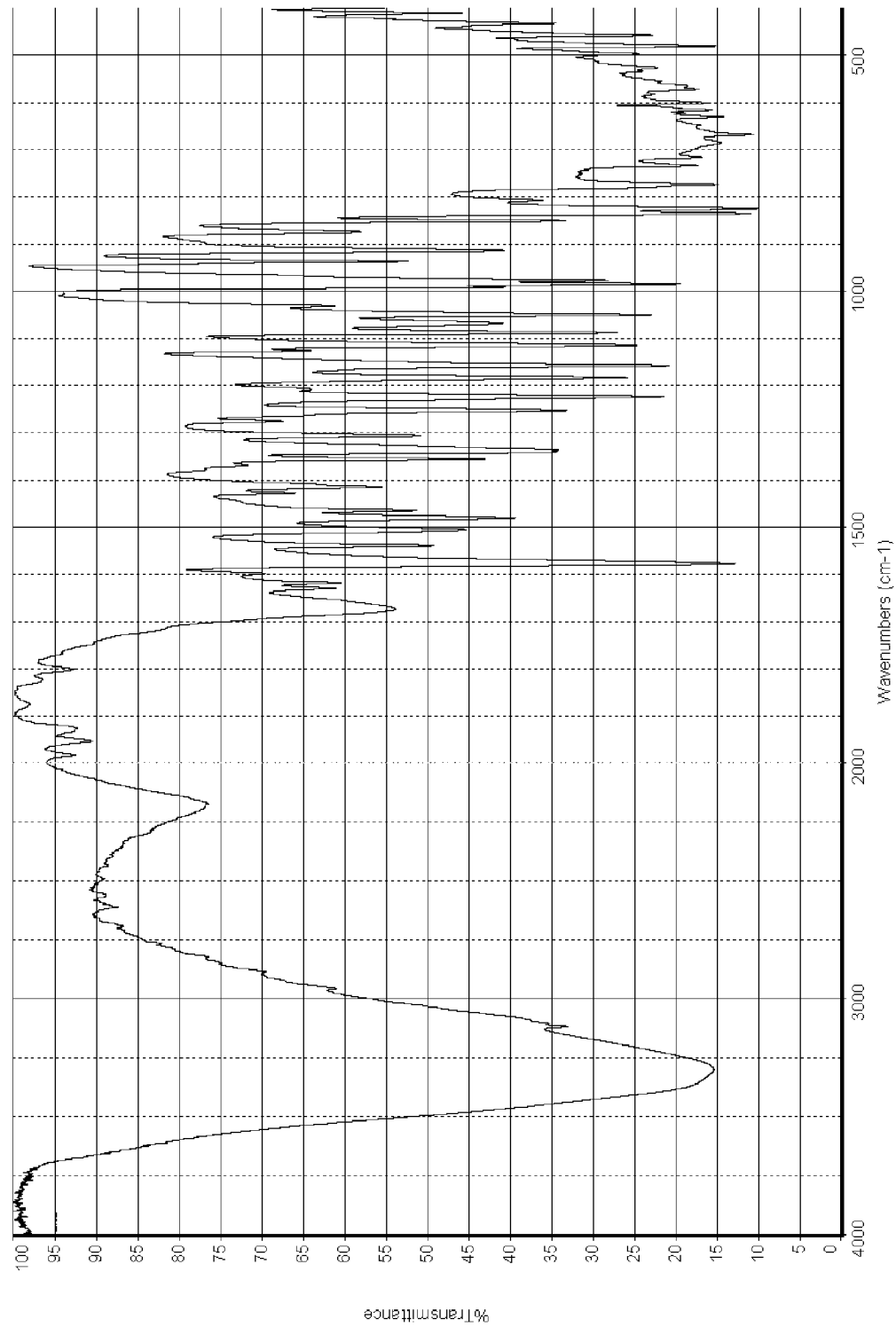
FIG. 6 illustrates IR spectrum for hydrate of compound of formula (I).

FIG. 6 provides exemplary IR spectra for the hydrate form.

The aqueous solubility of the hydrate form at different pH is summarised in Table 7 (see Example 4).

The hydrate form can be prepared by precipitating the compound of formula (I) from aqueous HCl at a concentration of about 0.1N and collecting the so-formed crystals.

Salts of Compound (I)

The present invention further contemplates salts of compound (I), more in particular its salts with hydrochloric acid, hydrobromic acid, methane sulphonic acid (mesylate salt), ethane sulphonic acid (esylate salt) or p-toluene sulphonic acid (tosylate salt), more preferably with hydrobromic acid, methane sulphonic acid, ethane sulphonic acid or p-toluene sulphonic acid.

As explained elsewhere in this specification, salts such as above may be obtained in the course of the synthesis of compound (I), and represent particularly advantageous intermediates thereof.

In addition, the present salts may also be obtained by treating the free base form of compound (I) with the corresponding acid, either neat or preferably in a solvent. In a preferred embodiment, the free base form of compound (I) can be dissolved in an alcohol, preferably in ethanol at an elevated temperature, and neutralised by addition of the acid thereto, and collecting the so-formed precipitate.

Select properties of the above salts are given in Examples 9 to 11.

Synthetic Processes

In a further aspect, the invention relates to new processes for the preparation of the compound of formula (I) or salts thereof. In particular, the first process involves reactions as described in Scheme 1 below and optionally and preferably the reactions to produce intermediates as disclosed in Schemes 2 and 3 and in section "Preferred synthetic routes". Benefits of the first process have been addressed and are further explained under the respective Schemes.

The second process is described in Scheme 5 below, and may optionally and preferably also involve reactions to produce intermediates as disclosed under Schemes 6 and 7 below. Benefits of the second process include inter alia, the avoidance of the carcinogenic and dangerous hydrazine and of the genotoxic intermediates 3-chloro-6-(1-methyl-1H-pyrazol-4-yl)pyridazine and 2,2-difluoro-2-quinolin-6-ylacetohydrazide from the reaction process.

During any of the processes for preparation of compound (I) according to the present invention, it may be necessary and/or desirable to protect sensitive or reactive groups on any of the molecules concerned. This may be achieved by means of conventional protecting groups, such as those described in Protecting Groups, P. Kocienski, Thieme Medical Publishers, 2000; and T. W. Greene & P. G. M. Wuts, Protective Groups in Organic Synthesis, 3rd ed. Wiley Interscience, 1999. The protecting groups may be removed at a convenient subsequent stage using methods known in the art.

The reactions of the synthetic methods claimed herein are carried out in suitable solvents which may be readily selected by one of skill in the art of organic synthesis, said suitable solvents generally being any solvent which is substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

After any of the reactions is carried out or after removing protecting group(s), intermediates and/or final compounds may, if necessary for the following steps and/or for monitoring the reaction, be worked-up and/or purified by methods known in the field of organic synthetic chemistry, such as filtering, solvent extraction, solvent evaporation by heat or under vacuum, re-crystallisation, trituration, chromatography or a method using an ion exchange resin.

Scheme 1

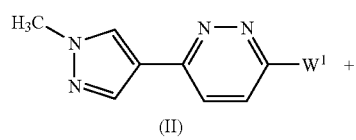

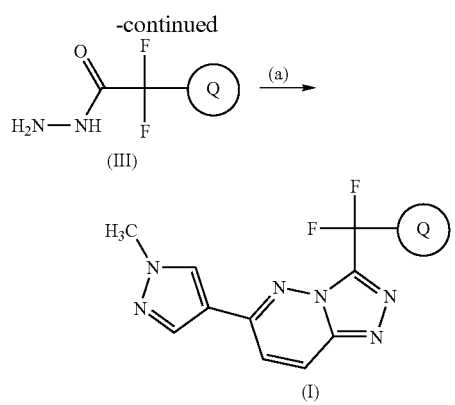

wherein:
$W^1$ is a leaving group
Q is quinolin-6-yl:

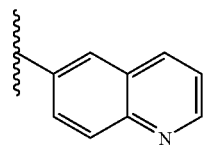 [SMILES: *c1ccc2ncccc2c1]

Scheme 1 illustrates the synthetic route (a) leading to the compound of formula (I). The route involves reacting pyridazine substituted in position 6 with 1-methyl-1H-pyrazol-4-yl and in position 3 with an appropriate leaving group $W^1$ (II) and 2,2-difluoro-2-quinolin-6-yl-acetohydrazide (III) to obtain the compound 6-{difluoro[6-(1-methyl-1H-pyrazol-4-yl)[1,2,4]triazolo[4,3-b]pyridazin-3-yl]methyl}quinoline (I).

In the present invention, the intermediates (II) and (III) are reacted in the presence of an acid. Therefore, the route (a) may be contemplated as comprising reactions referred to herein as (a') and (a"). A first reaction (a') yields a salt of the compound (I) with the acid employed in the reaction. In reaction (a") said salt can be treated with a suitable base to achieve free base form of the compound (I).

Leaving groups $W^1$ suitable for the above synthesis may be conventional as generally known to a skilled person. In a preferred embodiment, the leaving group $W^1$ may be selected from halogens, more preferably Cl, Br or I, and suitable sulphonate groups, more preferably OMs, OTs, OTf or benzenesulphonyloxy (—$OSO_2C_6H_5$). Other potentially useful leaving groups $W^1$ may include acetoxy (—OC(=O)$CH_3$), trifluoroacetoxy (—OC(=O)$CF_3$) and nitrooxy (—$ONO_2$). Preferably, the leaving group $W^1$ is halogen, more preferably Cl, Br or I. In an embodiment, the leaving group anion may be the same as the anion of the acid used in reaction (a').

The acid employed in the reaction (a') may preferably have pKa less than about 3, e.g., less than about 2.5, more preferably less than about 2, e.g., less than about 1.75, less than about 1.5 or less than about 1.25. Yet more preferably, the pKa of said acid may be equal or less than 1 (i.e., pKa ≤1), e.g., ≤0.8 or ≤0.6, still more preferably ≤0.4, e.g., ≤0.2 or ≤0, even more preferably ≤−0.2, e.g., ≤−0.4 or ≤−0.6 and very preferably ≤−0.8, e.g., ≤−1.0, ≤−1.2 or ≤−1.5. Particularly preferably, said acid may be a strong acid, i.e., having pKa less than about −1.79. The term "pKa" with reference to acids is established in the art and designates the logarithm of the reciprocal of the dissociation constant of an acid measured in water at 25° C. When said acid is a polybasic acid, at least one of its pKa can have the above preferred value. pKa values are listed, e.g., in Lange's Handbook of Chemistry (16th ed., by Speight J. G., McGraw-Hill, 2005).

In particularly preferred embodiments, the acid employed in the reaction (a') may be a hydrohalic acid, more preferably HCl or HBr, sulphuric acid ($H_2SO_4$), trifluoroacetic acid, or a sulphonic acid, more preferably p-toluene sulphonic acid, p-bromobenzene sulphonic acid, trifluoromethane sulphonic acid, camphor sulphonic acid, methane sulphonic acid or ethane sulphonic acid. Very preferably, said acid may be methane sulphonic acid, which greatly facilitates reaction (a').

The acid may be present in the reaction (a') in various quantities, such as, for example, ranging from about 0.1× or from about 0.25× or from about 0.5× or from about 0.75× molar equivalent relative to the intermediate (II) and/or (III) through molar excess over said intermediate(s). Preferably, the reaction may employ a molar excess of said acid over the intermediate (II) and/or (III), such as, without limitation, between about 1.1× and 10×, more preferably between about 1.1× and 5×, even more preferably between about 1.1× and 3×, still more preferably between about 1.1× and 2× or between about 1.1× and 1.5×, such as, e.g., about 1.2×, about 1.4×, about 1.6× or about 1.8× molar excess of said acid relative to the intermediate (II) and/or (III).

As noted earlier, inclusion of an acid in the reaction (a') can advantageously allow to lower the reaction temperature to less than 120° C., which may avoid unwanted side reactions of the intermediates (II) and/or (III) with an alcohol solvent as observed in the prior art. Hence, in preferred embodiments, the reaction (a') may be performed at a temperature lower than 120° C., e.g., ≤118° C., ≤116° C., ≤114° C., ≤112° C. or ≤110° C. Preferably, the reaction (a') may be performed at between about 50° C. and <120° C., more preferably between about 80° C. and <120° C., still more preferably between about 100° C. and <120° C., such as, e.g., between 50° C. and 115° C., or between 80° C. and 110° C.

The reaction (a') may be carried out in an appropriate solvent, preferably a suitable alcohol solvent. The term "alcohol" refers to organic compounds comprising one or more hydroxy groups —OH attached to saturated carbon atom(s). Alcohols may optionally comprise other functional groups, such as, e.g., alkyloxy groups. An appropriate alcohol solvent for use in reaction (a') is liquid at the reaction temperature, and preferably also at ambient temperature, and is capable of dissolving the intermediates (II) and (III) and/or allowing said intermediates to react at the reaction temperature. More preferably, reaction (a') may involve higher boiling alcohol solvents (e.g., having a boiling point equal to or higher than about 80° C.). Preferred examples include inter alia propanol, butanol, pentanol and 1-methoxy-2-propanol, the latter being particularly suitable. The inventors also realised that using secondary or tertiary alcohol solvents (e.g., isopropanol, sec-butanol, 1-methoxy-2-propanol, etc.) may, vis-à-vis primary alcohols, advantageously reduce unwanted side-reactions of the alcohol solvent with intermediates (II) and/or (III).

As already noted, the formation of a salt of compound (I) in the reaction (a'), in particular where the solvent is a suitable alcohol as above allowing for the precipitation of said salt there from (e.g., particularly preferably 1-methoxy-2-propanol) may afford for high yields and simple recovery of said precipitated salt from the reaction mixture, e.g., by filtration, centrifugation or decantation. This can advantageously provide the compound (I) salt at a satisfactory degree of purity while avoiding extensive work-up and extraction procedures.

Hence, a particularly preferred embodiment of the reaction (a') is illustrated in the reaction scheme (a'1):

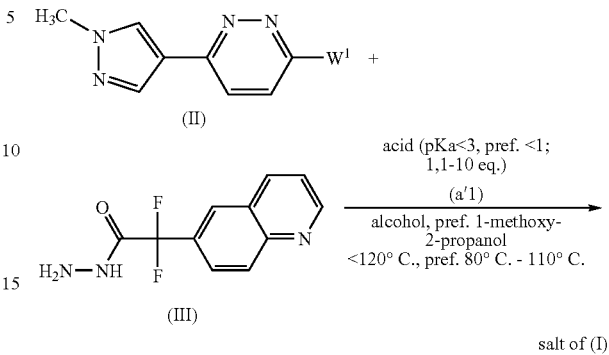

wherein $W^1$ is a leaving group as defined above

In the reaction (a") the salt of compound (I) obtained in the reaction (a') can be further converted to a free base form via treatment with sufficient amount of a suitable base. Suitable bases for this purpose are generally ones with comparably stronger basicity relative to the compound (I). Preferably, said bases may have pKa (of their conjugate acid) greater than about 7, e.g., greater than about 7.5, preferably greater than about 8, e.g., greater than about 8.5, and still more preferably greater than about 9. Exemplary bases include, by preference but without limitation, alkali metal hydroxides, preferably NaOH or KOH, carbonates, preferably $Na_2CO_3$ or $K_2CO_3$, ammonia and organic bases, preferably primary, secondary or tertiary amines, such as, e.g., benzylamine, methylamine, di- and tri-methylamine, ethylamine, di- and tri-ethylamine, ethylenediamine and diisopropylamine. Ammonia is particularly preferred.

Alkalisation of the salt of compound (I) with a base in reaction (a") may be performed under suitable conditions which are generally available to a skilled person. By means of illustration and not limitation, said salt may be reacted with a neat base. More preferably, the neutralisation may be performed in a suitable solvent capable of dissolving the salt of compound (I) and the base and/or allowing said salt and base to react. Even more preferably, the solvent may also allow for the precipitation of the free base form of compound (I) there from, thereby affording high yields and simple recovery of said precipitated compound (I), e.g., by filtration, centrifugation or decantation. Preferred solvents may include aqueous solvents, such as, e.g., water or mixtures of water with other water-miscible protic solvents, preferably with alcohols, e.g., methanol, ethanol, or isopropanol.

It shall be appreciated by a skilled person that the salts of compound (I) obtained in the reaction (a') or the free base form thereof obtained in reaction (a") can be further purified by one or more methods known in the field of organic synthesis chemistry, such as, e.g., solvent extraction, re-crystallisation, chromatography or methods using an ion exchange resin.

The above intermediates (II) and (III) may be obtained by methods known to those skilled in the art. The following reaction Schemes 2 and 3 are meant to illustrate non-limiting, albeit potentially preferred, examples of preparing said intermediates.

Scheme 2

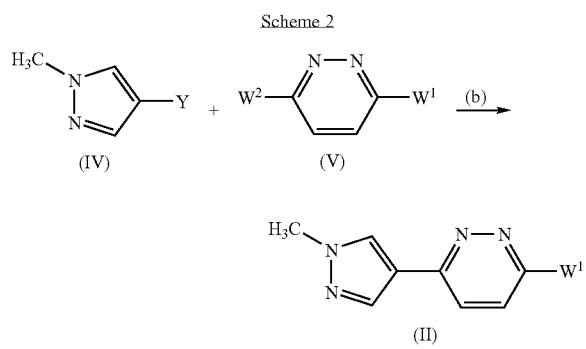

wherein:
$W^1$, $W^2$ are leaving groups
Y is a boronic species, zincate or stannane Scheme 2 illustrates an exemplary route taken to obtain the intermediate of formula (II), involving a transition-metal catalysed cross-coupling reaction (b) between pyridazine 3,6-disubstituted with leaving groups $W^1$ and $W^2$ (V) and a 1-methyl-1H-pyrazole-4-yl-substituted boronic species (such as, preferably but without limitation, boronic acid, boronic esters, haloborates including potassium trifluoroborate, or borane), zincate or stannane (IV), under, e.g., Suzuki (Miyaura N., Suzuki A. 1995. Chem. Rev. 95: 2457), Negishi (Negishi E. et. al. 1977. J. Org. Chem. 42: 1821) or Stille (Stille J. K. 1986. Agnew. Chem., Int. Ed. Engl. 25: 508, and references therein) conditions.

Cross-coupling reactions (b) may be generally performed in an inert environment mediated by a catalyst, such as, e.g., Pd(PPh$_3$)$_4$, PdCl$_2$(PPh$_3$)$_2$, Pd(dppf)Cl$_2$, Pd/C, Pd(OAc)$_2$ or a Peppsi-iPr catalyst (Organ M. G. et al. 2006. Chemistry—A European Journal 12(18): 4743-4748, and references therein). Where applicable, the compound of formula (IV), particularly a boronic species, may be activated, for example by a suitable base, such as, e.g., Na$_2$CO$_3$, K$_2$CO$_3$, NaOCH$_2$CH$_3$, CsF, N(CH$_2$CH$_3$)$_3$, NaOAc, KOAc, DIPEA or K$_3$PO$_4$. These reactions may generally occur at temperatures ranging from about 60° C. to about 150° C. in polar aprotic solvents (e.g., THF, 2-methyl THF, DMF, DMA) or biphasic solutions.

The leaving group $W^1$ is as elaborated under Scheme 1 above. Leaving groups $W^2$ suitable for cross-coupling reactions (b) are generally known to a skilled person. Preferably, the leaving group $W^2$ may be selected from halogens and perfluorinated sulphonates, more preferably from I, Br, Cl and OTf, and even more preferably from I, Br and OTf. Leaving groups $W^1$ and $W^2$ may be the same or different.

Where the boronic species, zincate or stannane of formula (IV) is not commercially available, it can be synthesised from the corresponding halide or by direct metallation/transmetallation procedures. An exemplary, non-limiting commercially available boronic species of formula (IV) useful in the present method is 1-methyl-1H-pyrazole-4-boronic acid pinacol ester (Sigma-Aldrich Cat. No. 595314; Xu G. & Gilbertson S R. 2005. Org. Lett. 7: 4605-4608).

Scheme 3

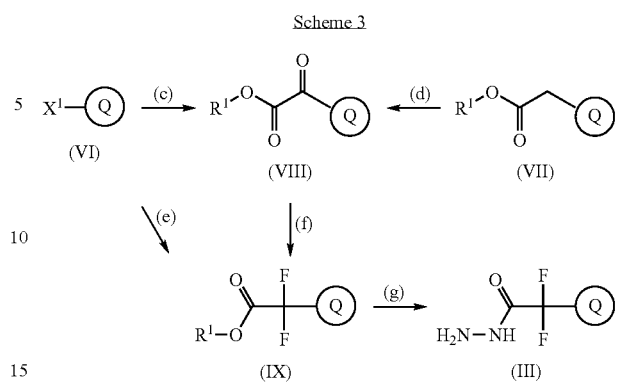

wherein:
$X^1$ is Cl, Br or I
$R^1$ is $C_{1-6}$ alkyl
Q is quinolin-6-yl:

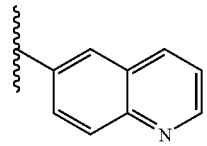

Scheme 3 illustrates exemplary routes taken to obtain the intermediate of formula (III).

The routes comprise reaction (g) which involves contacting the $C_{1-6}$ alkyl difluoro(quinolin-6-yl)acetate (IX), wherein $R^1$ is $C_{1-6}$ alkyl, preferably $C_{1-4}$ alkyl, more preferably $C_{1-3}$ alkyl, and even more preferably methyl or ethyl, with hydrazine or hydrazine equivalent under conditions sufficient to produce the 2,2-difluoro-2-quinolin-6-yl-acetohydrazide (III).

The term "$C_{1-6}$ alkyl", alone or as part of another group, means a univalent branched or un-branched hydrocarbon radical of between 1 and 6, e.g., 1, 2, 3, 4, 5 or 6, carbon atoms, such as for example methyl, ethyl, propyl, butyl, 2-methylpropyl, pentyl, hexyl and the like. $C_{1-6}$ alkyl groups also particularly encompass $C_{1-4}$ alkyl groups, more particularly $C_{1-3}$ alkyl groups, and even more particularly methyl and ethyl moieties. The term "$C_{1-4}$alkyl", alone or as part of another group, means a univalent branched or un-branched hydrocarbon radical of between 1 and 4, e.g., 1, 2, 3 or 4, carbon atoms, such as for example methyl, ethyl, propyl, butyl, 2-methyl-propyl and the like. The term "$C_{1-3}$alkyl", alone or as part of another group, means a univalent branched or un-branched hydrocarbon radical of between 1 and 3, e.g., 1, 2 or 3, carbon atoms, such as for example methyl, ethyl, propyl.

Hydrazine equivalents for reaction (g) include anhydrous hydrazine, hydrazine hydrate, as well as salts of hydrazine, such as, e.g., hydrazine acetate, hydrazine hydrobromide, hydrazine hydrochloride and hydrazine hemisulphate. Preferably, hydrazine hydrate may be employed. It is understood that when hydrazine salts are used, an additional quantity of base, such as sodium hydroxide or sodium carbonate, may be needed to neutralise the acids of the hydrazine salts. Typically, the reaction may employ a molar excess of hydrazine or hydrazine equivalent, such as, without limitation, between 1.2× and 20×, more preferably between 1.5× and 10×, even more preferably between 2.0× and 5×, such as, for example, about 2.5×, about 3.0×, about 3.5×, about 4.0× or about 4.5× molar excess of hydrazine or hydrazine equivalent relative to compound (IX).

The reaction (g) may generally take place at temperatures between RT and the reflux temperature of the solvent, e.g., at about ambient temperature, in alcohol solvents, such as, e.g., methanol, ethanol, propanol, methoxypropanol, butanol or amylene hydrate (2-methyl-2-butanol). The inventors realised that amylene hydrate may be particularly advantageous, as it allows high yields and simple recovery of the precipitated product (III) from the reaction mixture, e.g., by filtration, centrifugation or decantation.

Hence, a particularly preferred embodiment of the reaction (g) is illustrated in the reaction scheme (g1):

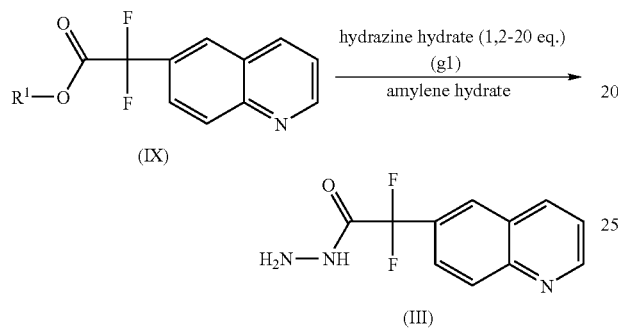

wherein:
$R^1$ is $C_{1-6}$ alkyl as defined above

Reactions (e) and (f) depict alternative routes to arrive at the intermediate of formula (IX). The reaction (e) involves copper mediated cross-coupling of the 6-haloquinoline (VI), wherein $X^1$ is Cl, Br or I, preferably Br or I, more preferably I, with a $C_{1-6}$ alkyl halo(difluoro)acetate of formula $R^1OC(=O)CF_2X^2$, wherein $R^1$ is as above and $X^2$ is Cl, Br or I, preferably Br or I, more preferably Br. The reaction (e) may typically be performed in an inert environment, mediated by a copper catalyst, e.g., Cu (0) (nano)powder, in a polar aprotic solvent, such as DMSO. Also particularly contemplated is a manner in which the active copper species is generated in-situ from copper(II)sulphate and the sodium salt of ascorbic acid.

In the reaction (f) the $C_{1-6}$ alkyl oxo(quinolin-6-yl)acetate (VIII), wherein $R^1$ is as above, is deoxofluorinated to yield the intermediate (IX). The reaction generally involves contacting the compound (VIII) with art-known deoxofluorinating agents including inter alia DAST (preferably diethyl-DAST), Deoxo-Fluor™ (Lal S et al. 1999. J. Org. Chem.: 7048-7054) or sulphur tetrafluoride ($SF_4$), in a suitable non-aqueous solvent such as, e.g., methylene chloride, chloroform, trichlorofluoromethane, glyme or diglyme. The carbonyl to geminal difluoride transformation (f) may be typically performed at room temperature or higher.

In a preferred embodiment, the deoxofluorination reaction (f) may be performed using $SF_4$ in the presence of a Lewis acid catalyst, preferably HF. Preferably, the reaction may employ a molar excess of $SF_4$, such as, without limitation, between 1.5× and 20×, preferably between 2.0× and 10×, more preferably between 2.5× and 5×, such as, e.g., about 3.0×, about 3.5×, about 4.0× or about 4.5× molar excess of $SF_4$ relative to compound (VIII). The reaction may preferably also use a molar excess of HF, such as, without limitation, between 1.1× and 5×, preferably between 1.1× and 3×, more preferably between 1.5× and 2.5×, such as, e.g., about 1.7×, about 2.0× or about 2.3× molar excess of HF relative to compound (VIII). The $SF_4/HF$-mediated deoxofluorination reaction may be effected in an appropriate non-aqueous solvent, e.g., as listed above, preferably in methylene chloride, preferably between ambient temperature and about 60° C., more preferably between about 30° C. and about 60° C., or between about 35° C. and about 50° C., e.g., at about 40° C. or at about 45° C.

Accordingly, a particularly preferred embodiment of the reaction (f) is illustrated in the reaction scheme (f1):

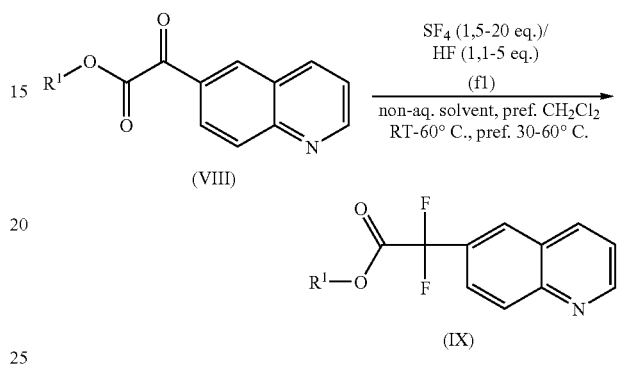

wherein:
$R^1$ is $C_{1-6}$ alkyl as defined above

Reactions (c) and (d) depict alternative routes to arrive at the intermediate of formula (VIII). The reaction (d) involves oxidation of the $C_{1-6}$ alkyl quinolin-6-ylacetate (VII), wherein $R^1$ is as above, to the $C_{1-6}$ alkyl oxo(quinolin-6-yl) acetate of formula (VIII). The reaction may employ agents appropriate for oxidation of active methylene groups in carbonyl compounds, such as, e.g., selenium dioxide ($SeO_2$) in a suitable solvent, for example dioxane.

The reaction (c) may advantageously involve preparing a Grignard complex of the 6-haloquinoline (VI), wherein $X^1$ is Cl, Br or I, preferably Br or I, more preferably I, and reacting said complex with molar excess of oxalate derivative of formula $R^1OC(=O)C(W^3)=O$, wherein $R^1$ is as above and $W^3$ is a leaving group.

Preparation of Grignard reagents of heteroarylhalides is generally known in the art and may typically involve reacting a heteroarylhalide, such as herein the 6-haloquinoline (VI), with a reagent such as Mg (0) (for example, Mg turnings or powder), iPrMgBr, iPrMgCl or iPrMgCl.LiCl, typically added in excess of from about 1.05 to about 2 molar equivalents relative to the halogen compound; in an appropriate ether solvent, such as, e.g., THF, 2-methylTHF, diethyl ether, tert-butyl methyl ether or dimethoxyethane; and advantageously at temperature below 0° C., e.g., between 0° C. and −80° C. The resulting solution or suspension of the Grignard reagent can, optionally following removal of excess Mg, be used in the next stage without further work-up.

The Grignard reagent of the 6-haloquinoline (VI) is hence reacted with a molar excess of the oxalate derivative $R^1OC(=O)C(W^3)=O$ to obtain the compound (VIII). The molar excess of said oxalate derivative may be, without limitation, between 1.5× and 20×, preferably between 2.0× and 10×, more preferably between 2.5× and 5×, such as, e.g., about 3.0×, about 3.5×, about 4.0× or about 4.5× molar excess relative to the compound (VIII). This reaction may be advantageously performed in an ether solvent as above, commonly the same solvent as used to prepare the Grignard reagent. Also advantageously, the reaction may be carried out at temperature below 0° C., e.g., between 0° C. and −80° C. Following adequate reaction time, the reaction may be advantageously quenched using appropriate quenching agents known per se, such as, e.g., NH₄OAc or preferably NH₄Cl.

Appropriate leaving groups $W^3$ will be understood by the skilled person, and may preferably include Cl, OC(=O)R², —OR² or —NR²R³, wherein R² and R³ are each independently $C_{1-6}$ alkyl, preferably $C_{1-4}$ alkyl, more preferably $C_{1-3}$ alkyl, and even more preferably methyl or ethyl. Preferably, $W^3$ is —OR², i.e., the oxalate derivate is a dialkyloxalate R¹OC(=O)C(OR²)=O, wherein R¹ and R² are each independently $C_{1-6}$ alkyl, preferably $C_{1-4}$ alkyl, more preferably $C_{1-3}$ alkyl, and even more preferably methyl or ethyl. Preferably, R¹ and R² in said dialkyloxalate may be the same, such as, e.g., dibutyloxalate, dimethyloxalate or diethyloxalate.

The inventors have also determined particularly advantageous conditions to be employed in the reaction (c) to ensure high yields of the intermediate (VIII). In particular, the Grignard reagent may be preferably prepared from 6-iodoquinoline using iPrMgCl·LiCl in THF. Preferred temperature ranges between 0° C. and −60° C., more preferably between −10° C. and −40° C., such as, e.g., about −20° C. or about −30° C. The resulting Grignard complex is added to molar excess (as above) of diethyloxalate in THF. The temperature of this reaction is preferably between 0° C. and −60° C., more preferably between −20° C. and −50° C., such as, e.g., about −30° C. or about −40° C. The reaction can be appropriately quenched, preferably using NH₄Cl.

Accordingly, a particularly preferred embodiment of the reaction (c) is illustrated in the reaction scheme (c1):

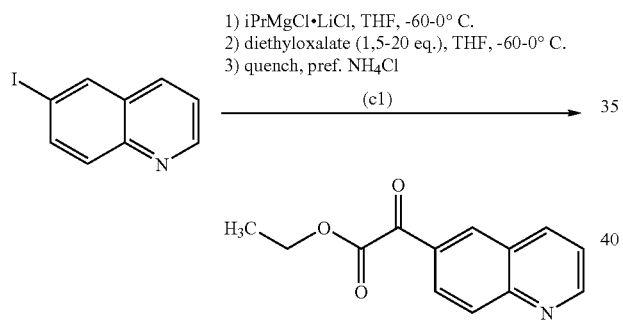

Preferred Synthetic Routes

As mentioned, the invention obtains salts or the free base form of compound (I) by reacting the intermediates (II) and (III) in the presence of an acid, which allows for considerable advantages, such as, e.g., improved yield and simplified purification of the desired product.

Whereas the intermediates (II) and (III) may be in principle obtained by any methods available to a skilled person (reference is also made to WO2007/075567), the preceding Schemes 2 to 3 detail preferred options which provide advantages that can further improve the overall synthetic process, e.g., yield and/or purity of the product, and/or the easiness and/or upscalability of the process.

Accordingly, in preferred embodiments, a process for preparing a salt or the free base form of compound (I) according to the invention may further comprise:
  reaction (b) as above to prepare the intermediate (II) from the compounds (IV) and (v); and/or
  reaction (g) as above, preferably employing conditions as defined for the reaction (g1) above, to prepare the intermediate (III) from the intermediate (IX); and/or
  reaction (f) as above, preferably employing conditions as defined for the reaction (f1) above, to prepare the intermediate (IX) from the intermediate (VIII); and/or
  reaction (c) as above, preferably employing conditions as defined for the reaction (c1) above, to prepare the intermediate (VIII) from the 6-haloquinoline (VI).

Hence, in particularly preferred embodiments, a process for preparing a salt or the free base form of compound (I) may proceed along the following Scheme 4.

Scheme 4

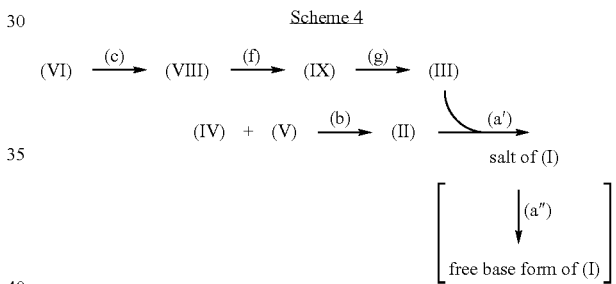

wherein all numerals and letters depict compounds and reactions as taught above, respectively; the inclusion of reaction (a″) in box brackets indicates that this step may be included optionally.

In an even more preferred embodiment, the route from the 6-haloquinoline (VI) to the intermediate (III) in Scheme 4 may involve the sequence of reactions (c1), (f1) and (g1) as detailed above.

Scheme 5

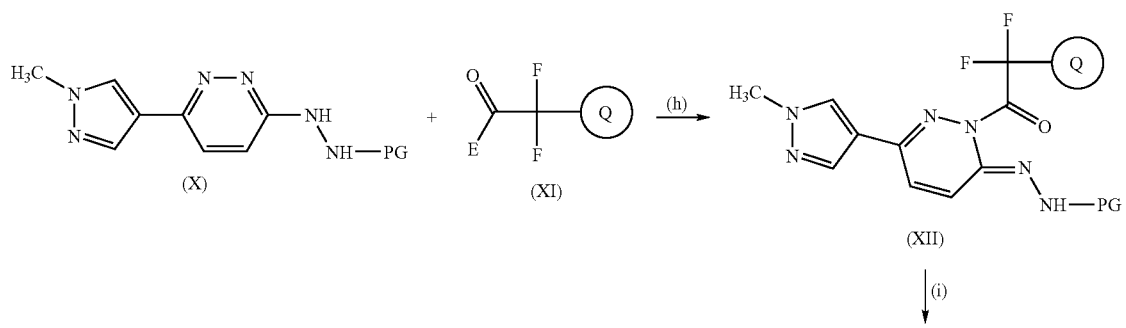

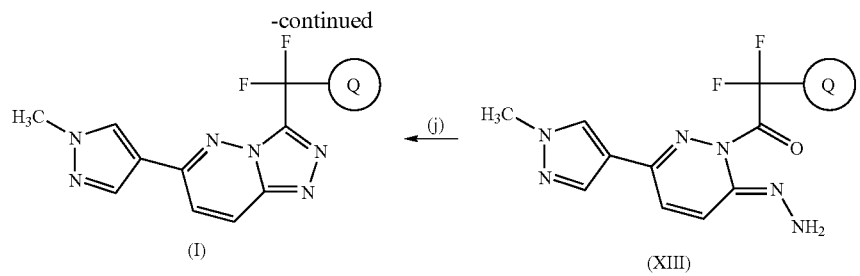

wherein:
PG is a protecting group
E is —OH, —O$^{(-)}$M$^{(+)}$, or —OR$^1$, wherein M is alkali metal and R$^1$ is C$_{1-6}$ alkyl
Q is quinolin-6-yl:

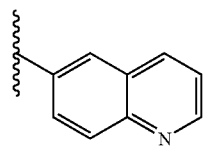 [SMILES: *c1ccc2ncccc2c1]

Scheme 5 illustrates alternative synthetic route leading to the compound of formula (I).

The route comprises reaction (h) which involves reacting pyridazine substituted in position 6 with 1-methyl-1H-pyrazol-4-yl and in position 3 with protected (PG, see Scheme 6) hydrazino moiety (X) and the carboxyl compound (XI), or optionally a reactive functional derivative of said carboxyl compound (XI), such as, e.g., carbonyl imidazole derivative (imidazolide), acyl halide (such as, e.g., acyl chloride or bromide), mixed anhydride, 2-chloropyridinium or 3-chloroisoxazolium derivative, thioester or the like.

The carboxyl compound (XI) may preferably be a carboxylic acid (i.e., E is —OH), an alkali metal carboxylate salt (i.e., E is —O$^{(-)}$M$^{(+)}$, wherein M is alkali metal, preferably Na$^+$ or K$^+$, see Scheme 7) or an ester (i.e., E is —OR$^1$, wherein R$^1$ is C$_{1-6}$ alkyl, preferably C$_{1-4}$ alkyl, more preferably C$_{1-3}$ alkyl, even more preferably methyl or ethyl, see compound (IX)). In a preferred embodiment, said compound (XI) may be an alkali metal salt.

Reaction conditions to perform acylation (h) may be as generally known in the art. For example, a reactive acylating species of the carboxyl compound (XI) may be formed using a suitable halogenating agent, such as thionyl chloride, phosphorus trichloride, phosphorus pentachloride, phosphorus oxychloride or oxalyl chloride, preferably thionyl chloride; carbonyldiimidazole; 2-chloro-1-methylpyridinium; S-pyridin-2-yl chlorothiocarbonate; or the like, optionally in the presence of a catalyst such as 4-dimethylaminopyridine (DMAP); in an appropriate solvent, such as a suitable polar aprotic solvent, e.g., acetonitril. One skilled in the art can choose appropriate reagents and conditions of reaction (h) to ensure the integrity of the remaining portions of the reactants, in particular the N-PG bond.

The PG-protected intermediate (XII) is subsequently deprotected in reaction (i) to obtain the hydrazono compound (XIII). Precise conditions for N-deprotection depend on the nature of the protecting group PG, and are well described in literature, such as Greene & Wuts (supra). By means of example and not limitation, tBoc (tert-butoxycarbonyl) group may be removed by acid hydrolysis, Cbz (carbobenzyloxy) groups by hydrogenation, trifluoroacetyl groups by hydrolysis under mild conditions and benzenesulphonyl groups by photo-activated desulphonylation.

In a preferred embodiment, the protecting group PG may be tBoc. Removal of this group by acids hydrolysis (i) affords a salt of the hydrazono compound (XIII) which can advantageously precipitate from the reaction mixture, thereby allowing for increased yields and simple recovery, e.g., by filtration, centrifugation or decantation. Acids used for tBoc hydrolysis may be advantageously chosen from acids as defined under Scheme 1, preferably from hydrohalic acids, more preferably HCl or HBr, sulphuric acid, trifluoroacetic acid, or a sulphonic acid, more preferably p-toluene sulphonic acid, p-bromobenzene sulphonic acid, trifluoromethane sulphonic acid, camphor sulphonic acid, methane sulphonic acid or ethane sulphonic acid. Preferably, said acid may be methane sulphonic acid.

The intra-molecular cyclisation reaction (j) converts the hydrazono intermediate (XIII) to compound (I). The reaction may be effected at elevated temperatures, e.g., between 50° C. and the reflux temperature of a solvent, such as, e.g., between 60° C. and 110° C. Suitable solvents may include higher boiling alcohols, e.g., propanol, butanol, pentanol, preferably 1-methoxy-2-propanol. Optionally, formed water may be azeotropically distilled-off or removed using a water-abstracting agent.

If the compound (I) is formed as a salt (e.g., when PG removal involves acid hydrolysis), the free base form of (I) can be liberated with a suitable base, as described in reaction (a") under Scheme 1 above.

The above intermediates (X) and (XI) may be obtained by methods known to those skilled in the art. The following reaction schemes 6 and 7 are meant to illustrate non-limiting, albeit potentially preferred, examples of preparing said intermediates.

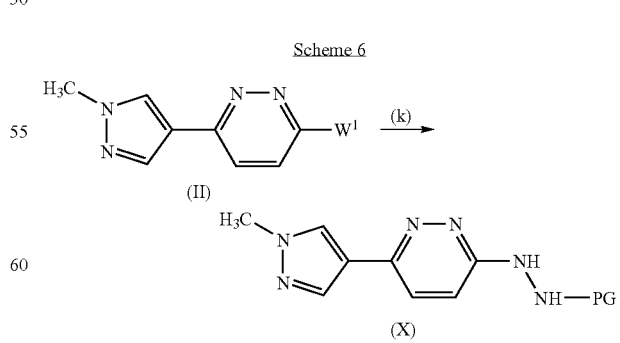

Scheme 6 wherein:
W$^1$ is a leaving group
PG is a protecting group

Scheme 6 illustrates a synthetic route (k) leading to the intermediate of formula (X). The route involves reacting the pyridazine derivative (II) as taught under Scheme 1 above with a hydrazine derivative of the formula $NH_2NHPG$, wherein PG is an appropriate nitrogen protecting group.

The term "nitrogen protecting group" refers to a group placed on a nitrogen atom for purposes of protecting an intermediate from an undesired reaction of said atom with a reagent. Suitable nitrogen protecting groups for use herein may be conventional amine protecting groups, which are commonly also appropriate for protecting hydrazine nitrogen, such as known in the art (e.g., T. W. Greene & P. G. M. Wuts, "Protective Groups in Organic Synthesis", 3rd ed., Wiley Interscience, 1999). Exemplary nitrogen protecting groups PG include, by preference but without limitation, moieties such as tBoc (tert-butoxycarbonyl), Cbz (carbobenzyloxy), aryl-substituted Cbz, trifluoroacetyl and benzenesulphonyl. Introduction of nitrogen protecting groups is well known in the art. In addition, protected hydrazine derivatives are commercially available (e.g., Boc-hydrazide: Fluka Cat. No. 19740; Cbz-hydrazine: Fluka Cat. No. 17307).

Typically, the reaction (k) may employ a molar excess of the hydrazine derivative such as, without limitation, between 1.2× and 20×, more preferably between 1.5× and 10×, even more preferably between 2.0× and 5×, such as, for example, about 2.5×, about 3.0×, about 3.5×, about 4.0× or about 4.5× molar excess of the hydrazine derivative relative to compound (II). The reaction (k) may generally take place at temperatures between RT and the reflux temperature of the solvent, in alcohol solvents, such as, e.g., propanol, 2-propanol, preferably 1-butanol.

Scheme 7

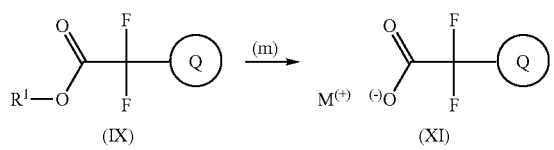

wherein:
$R^1$ is $C_{1-6}$ alkyl
M is an alkali metal
Q is quinolin-6-yl:

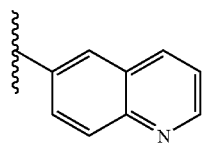 [SMILES: *c1ccc2ncccc2c1]

Scheme 7 illustrates an exemplary route taken to obtain a carboxylate salt derivative of formula (XI), wherein E is $-O^{(-)}M^{(+)}$, and M is alkali metal, preferably $Na^+$ or $K^+$, involving hydrolysis under basic conditions (saponification) (m) of the ester derivative (IX). The ester derivative (IX) may be generally as taught under Scheme 3, $R^1$ being $C_{1-6}$ alkyl, preferably $C_{1-4}$ alkyl, more preferably $C_{1-3}$ alkyl, and even more preferably methyl or ethyl.

Conditions of base-catalysed ester hydrolysis are well-known to a skilled person and typically involve reacting an ester, herein the intermediate (IX), with an aqueous base, preferably an alkali metal hydroxide, more preferably NaOH or KOH. Suitable aqueous solvents include, e.g., water and mixtures of water with other water-miscible protic solvents, preferably with alcohols, e.g., methanol, ethanol, or isopropanol. The reaction may be commonly performed at elevated temperatures, e.g., up to the reflux temperature of the solvent.

Pharmaceutical Formulations and Uses of the Polymorphic or Hydrate Forms and Salts of the Compound of Formula (I)

The active agents (i.e., as used in the following description, the polymorphic forms, hydrate form or salts of the compound of formula (I), or any mixtures thereof, as disclosed herein) of the invention can be used to inhibit tyrosine kinase activity or expression, including c-Met activity, reduce kinase activity or expression, including c-Met activity, and modulate expression of c-Met in a cell or a subject, or to treat a disorder related to c-Met kinase activity or expression in a subject. Inhibition of c-Met activity is believed to indirectly modulate c-Met expression.

In one embodiment to this aspect, the present invention provides a method for reducing or inhibiting the kinase activity of c-Met, and modulate expression of c-Met in a cell comprising the step of contacting the cell with an active agent of the invention. The present invention also provides a method for reducing or inhibiting the kinase activity of c-Met, and modulate expression of c-Met in a subject comprising the step of administering an active agent of the invention to the subject. The present invention further provides a method of inhibiting cell proliferation in a cell comprising the step of contacting the cell with an active agent of the invention.

The kinase activity or expression of c-Met in a cell or a subject can be determined by procedures well known in the art, such as the c-Met kinase assay described herein. Inhibition of c-Met kinase activity in cells can also be measured by determining the level of c-Met phosphorylation using an ELISA assay format or by Western Blotting.

The term "subject" as used herein, refers to an animal, preferably a mammal, most preferably a human, who has been the object of treatment, observation or experiment. The term "contacting" as used herein, refers to the addition of active agent to cells such that the active agent is taken up by the cell. In other embodiments to this aspect, the present invention provides both prophylactic and therapeutic methods for treating a subject at risk of (or susceptible to) developing a cell proliferative disorder or a disorder related to c-Met. Such disorders include pre-existing conditions related to c-Met expression (or over expression) and/or c-Met mutation.

In one example, the invention provides methods for preventing in a subject a cell proliferative disorder or a disorder related to c-Met, comprising administering to the subject a prophylactically effective amount of a pharmaceutical composition comprising an active agent of the invention and a pharmaceutically acceptable carrier.

Administration of said prophylactic agent can occur prior to the manifestation of symptoms characteristic of the cell proliferative disorder or disorder related to c-Met, such that a disease or disorder is prevented or, alternatively, delayed in its progression.

In another example, the invention pertains to methods of treating in a subject a cell proliferative disorder or a disorder related to c-Met comprising administering to the subject a therapeutically effective amount of a pharmaceutical composition comprising an active agent of the invention and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorder related to c-Met.

In another example, the invention pertains to methods of modulating in a subject a cell proliferative disorder or a disorder related to c-Met, such that modulation of the level of c-Met expression or of c-Met activity may act to ameliorate the cell proliferative disorder or a disorder related to c-Met, comprising administering to the subject a therapeutically effective amount of a pharmaceutical composition comprising an active agent of the invention and a pharmaceutically acceptable carrier.

The term "prophylactically effective amount" refers to an amount of an active agent or pharmaceutical agent that inhibits or delays in a subject the onset of a disorder as being sought by a researcher, veterinarian, medical doctor or other clinician. The term "therapeutically effective amount" as used herein, refers to an amount of active agent or pharmaceutical agent that elicits the biological or medicinal response in a subject that is being sought by a researcher, veterinarian, medical doctor or other clinician, which includes alleviation of the symptoms of the disease or disorder being treated. Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to c-Met", or "disorders related to c-Met receptor tyrosine kinase" shall include diseases associated with or implicating c-Met activity, for example, the overactivity of c-Met, and conditions that accompany these diseases. The term "overactivity of c-Met" refers to either 1) c-Met expression in cells which normally do not express c-Met; 2) c-Met activity by cells which normally do not possess active c-Met; 3) increased c-Met expression leading to unwanted cell proliferation; or 4) mutations leading to constitutive activation of c-Met. Examples of "disorders related to c-Met" include disorders resulting from over stimulation of c-Met due to abnormally high amount of c-Met or mutations in c-Met, or disorders resulting from abnormally high amount of c-Met activity due to abnormally high amount of c-Met or mutations in c-Met. It is known that overactivity of c-Met has been implicated in the pathogenesis of a number of diseases, such as cell proliferative disorders, neoplastic disorders and cancers.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. Cell proliferative disorders include neoplastic disorders (as used herein, a "neoplastic disorder" refers to a tumor resulting from abnormal or uncontrolled cellular growth) and other cell proliferative disorders.

Examples of cell proliferative disorders related to c-Met, include tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—including leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma)—and diseases associated with the formation of new vasculature, such as rheumatoid arthritis, and retinopathy.

Other cell proliferative disorders in which overactivity of c-Met has been implicated in their pathogenesis include cancers in which c-Met activity contributes to the invasive/metastatic phenotype, including cancers in which c-Met is not overexpressed or otherwise altered. In a further embodiment to this aspect, the invention encompasses a combination therapy for treating or inhibiting the onset of a cell proliferative disorder or a disorder related to c-Met in a subject. The combination therapy comprises administering to the subject a therapeutically or prophylactically effective amount of an active agent of the invention, and one or more other anti-cell proliferation therapy including chemotherapy, radiation therapy, gene therapy and immunotherapy. In an embodiment of the present invention, the active agent of the invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, 5-fluoro-deoxyuridine-monophosphate (5FdUMP), leucovorin, gemcitabine, capecitabine); alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, caminomycin, daunomycin); antimetabolites (e.g., clofarabine, aminopterin, cytosine arabinoside, methotrexate, decitabine); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib, lapatinib, sunitinib, vandetanib, BIBW2992, 17-bromo-8,9,10,11,12,13,14,19-octahydro-20-methoxy-13-methyl-4,6-ethanediylidenepyrimido[4,5-b][6,1,12]benzoxadiazacyclopentadecine); farnesyltransferase inhibitors (e.g., tipifarnib); histone deacetylase inhibitors (e.g. N-hydroxy-2-[4-[[(1H-indol-3-ylmethyl)amino]methyl]-1-piperidinyl]-5-pyrimidinecarboxamide and its 2,2,2-trifluoroacetate (JNJ-26481585)); inhibitors of the ubiquitinproteasome pathway (e.g., bortezomib, Yondelis, N1-[2-(1H-indol-3-yl)ethyl]-N4-4-pyridinyl-1,4-benzenediamine (JNJ26854165)).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6): 449-67. Additionally, yet to emerge chemotherapeutic agents are contemplated as being useful in combination with the active agent of the invention.

In another embodiment of the present invention, the active agent of the invention may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the active agent of the invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'. In other embodiments of this invention, the active agent of the invention may be administered in combination with an immunotherapy. As used herein, "immunotherapy" refers to a therapy targeting particular protein involved in tumor development via antibodies specific to such protein, e.g. trastuzumab. For example, monoclonal antibodies against vascular endothelial growth factor have been used in treating cancers.

Where a second pharmaceutical is used in addition to an active agent of the invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the active agent of the invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

By way of example only, camptothecin compounds are advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

By way of example only, vinca alkaloids may be advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

By way of example only, anti-tumor nucleoside derivatives may be advantageously administered in a dosage of 200 to 2500 mg per square meter (mg/m2) of body surface area, for example 700 to 1500 mg/m2. 5-fluorouracil (5-FU) is commonly used via intravenous administration with doses ranging from 200 to 500 mg/m2 (preferably from 3 to 15 mg/kg/day). Gemcitabine is advantageously administered in a dosage of about 800 to 1200 mg/m2 and capecitabine is advantageously administered in about 1000 to 2500 mg/m2 per course of treatment.

By way of example only, alkylating agents may be advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg of body weight, for carmustine in a dosage of about 150 to 200 mg/m2, and for lomustine in a dosage of about 100 to 150 mg/m2 per course of treatment.

By way of example only, podophyllotoxin derivatives may be advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

By way of example only, anthracycline derivatives may be advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter (mg/m2) of body surface area, or as known in the art, if different. For example, trastuzumab is advantageously administered in a dosage of 1 to 5 mg/m2, particularly 2 to 4 mg/m2 per course of treatment.

Dosages may be administered, for example once, twice or more per course of treatment, which may be repeated for example every 7, 14, 21 or 28 days. The active agents of the invention can be administered to a subject systemically, for example, intravenously, orally, subcutaneously, intramuscular, intradermal, or parenterally. The active agents of the invention can also be administered to a subject locally. Non-limiting examples of local delivery systems include the use of intraluminal medical devices that include intravascular drug delivery catheters, wires, pharmacological stents and endoluminal paving. The active agents of the invention can further be administered to a subject in combination with a targeting agent to achieve high local concentration of the compound at the target site. The active agents of the invention may be formulated for fast-release or slow-release with the objective of maintaining the drugs or agents in contact with target tissues for a period ranging from hours to weeks.

The present invention also provides a pharmaceutical composition comprising an active agent of the invention in association with a pharmaceutically acceptable carrier. The pharmaceutical composition may contain between about 0.1 mg and 1000 mg, preferably about 100 to 500 mg, of the active agent of the invention, and may be constituted into any form suitable for the mode of administration selected. The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" Formulations include Formulations for both clinical and/or veterinary use. The present invention also provides a pharmaceutical composition comprising, depending on the mode of administration, from 0.05 to 99% by weight, more preferably from 0.1 to 70% by weight, even more preferably from 0.1 to 50% by weight of the active agent, and, from 1 to 99.95% by weight, more preferably from 30 to 99.9% by weight, even more preferably from 50 to 99.9% by weight of a pharmaceutically acceptable carrier, all percentages being based on the total weight of the composition.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release Formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of an active agent of the invention. The composition includes a slow release carrier (typically, a polymeric carrier) and an active agent of the invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of this invention. The active agent of the invention is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, sweeteners, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and an active agent of the invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the active agent of the invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 5 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preFormulation composition containing a homogeneous mixture of an active agent of the invention, or a pharmaceutically acceptable salt thereof. When referring to these preFormulation compositions as homogeneous, it is meant that the active ingredient is dispersed evenly throughout the composition so that the composition may be readily subdivided into equally effective dosage forms such as tablets, pills and capsules. This solid preFormulation composition is then subdivided into unit dosage forms of the type described above containing from 0.1 to about 1000 mg, in particular from 0.1 to about 500 mg, of the active agent of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, acetyl alcohol and cellulose acetate.

The liquid forms in which the active agent of the invention can be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, active agents of the invention may be administered in a single daily dose, or the total daily dosage may be administered in divided doses of two, three or four times daily. Furthermore, active agents of the invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier known to the skilled man. Liquids such as ethanol, glycerol, water and the like can be used for granulation purposes. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active agent for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The active agents of the invention may be administered on a regimen up to four or five or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The active agents of the invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The active agents of the invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administor.

The present invention provides a drug delivery device comprising an intraluminal medical device, preferably a stent, and a therapeutic dosage of an active agent of the invention. The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds that prevent inflammation and proliferation, may provide the most efficacious treatment for post-angioplasty restenosis.

Active agents of the invention can be incorporated into or affixed to the stent in a number of ways and in utilizing any number of biocompatible materials. In one exemplary embodiment, the agent is directly incorporated into a polymeric matrix, such as the polymer polypyrrole, and subsequently coated onto the outer surface of the stent. The agent elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the agent elutes from the matrix. Stents and methods for coating are discussed in detail in WIPO publication WO9632907, U.S. Publication No. 2002/0016625 and references disclosed therein.

The solution of the active agent of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Agent is preferably only affixed to the outer surface of the stent that makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the active agents of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restenosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis. See Schiele T M et. al., 2004, "Vascular restenosis—striving for therapy." Expert Opin Pharmacother. 5(11): 2221-32. Vascular smooth muscle cells (VSMC) express c-Met receptor. Exposure to hepatocyte growth factor, the ligand for c-Met, stimulates these cells to exhibit a migratory phenotype. See Taher et. al., Hepatocyte growth factor triggers signaling cascades mediating vascular smooth muscle cell migration. *Biochem Biophys Res Commun*. (2002) 298 (1):80-6; Morishita R, Aoki M, Yo Y, Ogihara T. Hepatocyte growth factor as cardiovascular hormone: role of HGF in the pathogenesis of cardiovascular disease. Endocr J. (2002) June; 49(3):273-84. Since VSMC migration from the media to the intima of arteries plays a role in the development of atherosclerosis and restenosis, antagonists of c-Met kinase activity are believed to present a viable therapeutic strategy in the treatment of these diseases.

Accordingly, the present invention provides a method for the treatment of disorders related to c-Met, including restenosis, intimal hyperplasia or inflammation, in blood vessel walls, comprising the controlled delivery, by release from an intraluminal medical device, such as a stent, of an active agent of the invention in therapeutically effective amounts.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the agents for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering active agents of the invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, an active agent of the invention can be administered with high local concentrations at or near a target site and thus treats the disorder at the target site more effectively. The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal. In the present invention, the targetable or accessible component might be the c-Met receptor as it is accessible and expressed on or near the target tissues.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No. 5,855,866 to Thorpe et al). Methods are known to those skilled in the art to produce and isolate antibodies against tumor (U.S. Pat. No. 5,855,866 to Thorpe et al., and U.S. Pat. No. 6,342,219 to Thorpe et al.).

Techniques for conjugating therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985). Similar techniques can also be applied to attach active agents of the invention to non-antibody targeting agents.

Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the active agents of the invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolysable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition comprising an effective amount of an active agent of the invention conjugated to a targeting agent and a pharmaceutically acceptable carrier.

The present invention further provides a method of treating of a disorder related to c-Met, particularly a tumor, comprising administering to a subject a therapeutically effective amount of an active agent of the invention conjugated to a targeting agent.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the active agents of the invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

EXAMPLES

Example 1

Polymorph Form I of Compound (I)

a. Preparation Process 1

The compound of formula (I) (3 g, pure by chromatography and dry) is refluxed in 2-propanol (30 mL) for at least 4 hours. After cooling to room temperature, the solids are filtered and dried at 50° C. to provide 2.1 g of Form I.

b. Preparation Process 2

The compound of formula (I) was brought (200 µl/well) as a 33% dichloromethane/67% methanol solution (≅7.5 mg/mL) in a well of a 96 well plate containing 0.5 mL glass insert vials. The plate was then evaporated to dryness under nitrogen leaving approximately 1.5 mg of amorphous solid remaining in the well. Next an ethyl acetate/dichloromethane mixture (50/50 v/v %) was dispensed in the well. The plate was then sealed using a Teflon coated rubber mat, sonicated for 15 minutes at 50° C. and then heated at 50° C. for 1 hour. After heating, the plate was allowed to equilibrate to room temperature and left at room temperature sealed overnight. The plate seal was then removed and the solvents were allowed to evaporate slowly to provide Form I.

c. Preparation Process 3

The methanesulphonate (mesylate) salt of the compound of formula (I) (13.1 g, is dissolved in methanol/water (50/50, vol/vol; 300 mL) at reflux. Sodium carbonate is added until pH>7. The mixture is cooled to room temperature, the solids are filtered, washed and dried at 50° C. to provide 9.75 g of Form I.

Exemplary XRPD pattern for Form I is shown in FIG. 1 and Table 1; IR spectrum in FIG. 2 and Table 2; DSC scan in FIG. 7.

Example 2

Polymorph Form III of Compound (I)

a. Preparation Process 1

Methanesulphonate (mesylate) salt of the compound of formula (I) (8.7 g) is dissolved in ethyl acetate/water mixture (50/50 vol/vol; 400 mL). Addition of sodium carbonate (2.5 g) liberates the free base form of the compound of formula (I) which crystallises from the solvent mixture. The solids are filtered, washed and dried at 50° C. to provide 6.53 g of Form III.

b. Preparation Process 2

The compound of formula (I) (0.5 g, pure by chromatography or crude) is crystallised from methanol/water mixture (50/50, vol/vol; 10 mL) or from ethanol/water mixture (50/50, vol/vol; 10 mL) at 60° C. The solids are filtered and dried at 50° C. to provide 0.44 g of Form III.

c. Preparation Process 3

The compound of formula (I) (100 mg, pure by chromatography) is precipitated from 0.01N HCl (50 mL) at 25° C. The solids are filtered and dried at 50° C. to provide a sample of Form III.

d. Preparation Process 4

A hydrate of the compound of formula (I) (10 mg, as prepared in Example 3) is heated to 115° C. for 1 hour, yielding Form III (not isolated).

e. Preparation Process 5

Form I of the compound of formula (I) (0.5 g, as prepared in Example 1) is heated at 60° C. in acetone/water mixture (50/50, vol/vol; 12 mL) for 1 hour. The solids are filtered and dried at 50° C. to provide 0.48 g of Form III.

Exemplary XRPD pattern for Form III is shown in FIG. 3 and Table 3; IR spectrum in FIG. 4 and Table 4; DSC scan in FIG. 9.

Example 3

Hydrate Form

Preparation Process

The compound of formula (I) (100 mg, pure by chromatography) is dissolved in 0.1 N HCl (25 mL) at 25° C. To a sample of 5 mL of this solution is added compound of formula I until precipitate forms (concentration: 15 mg/mL) followed by addition of the remaining part of the solution and stirring overnight. The solids are filtered and dried at 50° C. (for a limited time period) to provide the hydrate form.

Exemplary XRPD pattern for the hydrate form is shown in FIG. 5 and Table 5; IR spectrum in FIG. 6 and Table 6.

Example 4

Solubility

Solubility of polymorph Forms I and III and the hydrate form of the compound of formula (I) was tested in aqueous conditions at different pH values. Table 7 demonstrates good solubility of these forms and a superior solubility of Form I (values are in mg/ml).

TABLE 7

| Solvent | Form I | Form III | hydrate |
| --- | --- | --- | --- |
| 0.1 HCl | 1.3 | 0.97 | 0.81 |
| 0.01 HCl | 0.10 | 0.078 | 0.056 |

TABLE 7-continued

| Solvent | Form I | Form III | hydrate |
| --- | --- | --- | --- |
| pH2 | 0.43 | 0.13 | 0.065 |
| pH4 | 0.005 | 0.003 | 0.002 |
| pH6 | 0.003 | 0.001 | 0.001 |
| pH8 | 0.004 | 0.001 | 0.001 |
| pH10 | 0.003 | 0.002 | 0.001 |

Example 5

Stability of the Hydrate Form in Aqueous Environments

Aqueous suspension of the compound of formula (I) 16 mg/ml was stored at about 4° C. up to 9 days. Samples were taken after 1, 2 and 9 days of storage. The suspensions were spread over a paper filter and dried at room temperature for 2 hours. The obtained materials were analysed by XRPD.

While the starting material contained a mixture of polymorphic Forms I and III, the XRD patterns of the suspensions stored at 4° C. for 1 day, 2 days and 9 days were compatible with those of the hydrate form. Moreover, the hydrate remained stable in the aqueous medium for at least 9 days (XRD not substantially changed).

In addition, measurement of particle size by scanning electron microscopy (SEM) indicated that storage for 9 days at 4° C. had no effect on the particle size of the hydrate.

Example 6

Properties of Polymorph Form I of Compound (I)

Form I is not Hygroscopic

Adsorption and desorption of water at 25° C. at different conditions of relative humidity was investigated on about 10 mg Form I of compound of formula (I), by registering the weight change as a function of relative humidity.

During an initial drying step a weight loss of 0.05% was registered. The obtained dry product adsorbed up to 0.5% water depending on the atmospheric humidity, and showed no hygroscopic behaviour and remained crystalline during the test.

Crystallographic Stability of Form I

The stability of the crystal structure of polymorph Form I of the compound (I) was studied after storage of the compound in open conditions for a period of six weeks at room temperature (RT) under <5%, 56% and 75% relative humidity (RH) at 50° C., and at 40° C. and 75% RH.

The samples were analysed by TGA, DSC, XRPD and IR spectroscopy. The results are in Table 8.

TABLE 8

| condition | TGA <100° C. | TGA <240° C. | XRD | IR | DSC Max (° C.) | ΔH (J/g) | App. |
|---|---|---|---|---|---|---|---|
| 0 days | 0.12 | 0.36 | Cryst., Ref | Cryst., Ref | 201.0 | 101 | SY |
| RT/<5% RH | 0.74 | 0.75 | ~Ref | ~Ref | 200.1 | 124 | SY |
| RT/56% RH | 0.58 | 0.80 | ~Ref | ±Ref | 200.4 | 120 | SY |
| RT/75% RH | 0.25 | 0.57 | ~Ref | ±Ref | 200.1 | 121 | SY |
| 50° C. | 0.31 | 0.57 | ~Ref | ~Ref | — | — | SY |
| 40° C./75% RH | 0.33 | 0.48 | ~Ref | ~Ref | 200.5 | 119 | SY |

~Ref: identical with Form I reference;
Cryst.: crystalline;
—: no measurement;
SY: slightly yellow;
DSC Max (° C.): endothermic melting peak with a maximum at . . . ° C.

Polymorph Form I is crystallographically stable. No changes are observed after storage under the different conditions. The XRD patterns and DSC curves remain the same before and after storage. The IR spectra of the samples stored for six weeks at room temperature (RT) under 56% and 75% relative humidity (RH) contain some small extra signals (±Ref).

Chemical Stability of Form I

Chemical stability of Form I was tested in different open storage conditions for periods of 1, 4 and 8 weeks: 40° C./75% RH; 50° C.; RT/<5% RH; RT/56% RH; RT/75% RH and 0.3da ICH high intensity light. The compound was analysed after storage by HPLC and by visual inspection. The results are in Table 9.

TABLE 9

| condition | HPLC Sum of impurities (w/w %) 1 w | 4 w | 8 w | Appearance 1 week | 4 weeks | 8 weeks |
|---|---|---|---|---|---|---|
| Reference | 0.54 | — | — | slightly yellow | — | — |
| 0.3da ICH light | 0.55 | — | — | slightly yellow | — | — |
| 40° C./75% RH | 0.51 | 0.66 | 0.54 | slightly yellow | slightly yellow | slightly yellow |
| 50° C. | 0.56 | 0.59 | 0.54 | slightly yellow | slightly yellow | slightly yellow |
| RT/<5% RH | — | 0.62 | 0.53 | — | slightly yellow | slightly yellow |
| RT/56% RH | — | 0.53 | 0.53 | — | slightly yellow | slightly yellow |
| RT/75% RH | — | 0.53 | 0.77 | — | slightly yellow | slightly yellow |

Polymorph Form I was chemically stable in all investigated conditions.

Example 7

Slurry Conversions of Different Forms of the Compound (I)

Slurry Conversions on Form III and Mixtures Form III/Hydrate 20 mg Form III with 0.25 ml solvent (2-propanol; or 2-propanone/water (8/2, v/v); or methanol/water (8/2, v/v)) was deposited in a vial. For each solvent, 3 vials were prepared and stored each at different temperatures (4° C., RT, 40° C.) for two days. After storage, the slurry was spread on a paper filter, the solid fractions were collected and dried 2 hours at RT. In a further experiment, the Form III was seeded with the hydrate using methanol/water (8/2, v/v) as the solvent. The polymorphic composition was measured using XRPD. The results are in Table 10.

TABLE 10

| Condition | 4° C. | RT | 40° C. |
|---|---|---|---|
| 2-propanol | III | III | III |
| 2-propanone/water (8/2, v/v) | hy | hy | hy |
| methanol/water (8/2, v/v) | III | III | III |
| methanol/water (8/2, v/v) containing hydrate seeds | III | III | III |

III: Form III
hy: hydrate

For 2-propanol and methanol/water (8/2, v/v) no conversion was found, even after seeding with the hydrate form. In 2-propanone/water (8/2, v/v) a conversion into the hydrate form occurred at all tested temperatures.

Slurry Conversion on Mixtures of Form III and Form I 30 mg of mixture of Form III and Form I and 0.25 ml solvent (2-propanol; or ethanol/water (8/2, v/v)) were placed in a vial. For each solvent, 2 vials were prepared and stored each at different temperatures (RT, 70° C.) overnight. After storage, the slurry was spread on a paper filter, the solid fractions were collected and dried 2 hours at RT. The polymorphic composition was measured using XRPD. The results are in Table 11.

TABLE 11

| Condition | RT | 70° C. |
|---|---|---|
| 2-propanol | I | I |
| ethanol/water (8/2, v/v) | I | I* |

I: Form I
*low amount of product

If Form I was present in the sample, a polymorphic conversion of Form III into Form I occurred at RT and at elevated temperature. This conversion also occurred in water containing medium.

Together, the above data indicates that Form I is the most stable polymorph from RT up to 70° C. The presence of Form I seeding material increases the conversion rate into Form I. If a 2-propanone-water mixture is used at temperatures from 4° C. up to 40° C., a conversion into the hydrate form is found.

Example 8

Thermal Conversions of Different Forms of the Compound (I)

Form III or hydrate form were thermally treated in a DSC oven (heating rate 10° C./min) up to selected temperatures (isotherm for 1 min) using an open sample pan. The selected temperatures are for Form III: 110° C. and 170° C.; and for hydrate form: 70° C., 110° C. and 170° C. The polymorphic composition of the obtained fractions was measured by XRPD. Table 12 summarises XRPD patterns in DSC treated Form III. Table 13 summarises XRPD patterns in DSC treated hydrate

TABLE 12

| Condition | XRPD measured composition |
|---|---|
| starting Form III | Form III |
| up to 110° C. | Form III |
| up to 170° C. | Form I |

TABLE 13

| Condition | XRPD measured composition |
|---|---|
| starting hydrate | hydrate |
| up to 70° C. | hydrate + Form III |
| up to 110° C. | Form III |
| up to 170° C. | mainly Form I |

Example 9

Preparation and Properties of Salts of Compound (I)

Free base of compound (I) (3 g; 7.95 mmol) was dissolved in absolute ethanol (40 mL) and heated to 78° C. An acid (HCl 6M in 2-propanol, 2.0 ml (12 mmol); HBr 48% in water, 0.98 mL (8.75 mmol); methane sulphonic acid, 917 mg (9.54 mmol); ethane sulphonic acid, 1.05 g (9.54 mmol) or p-toluene sulphonic acid monohydrate (1.66 g (8.75 mmol)) was added to the hot reaction mixture. The reaction mixture was allowed to cool to room temperature. The resulting precipitate was filtered off, washed with ethanol and dried under vacuum at 60° C.

The obtained solids were analysed by acid titration, Karl-Fisher titration and HPLC. A physical characterisation was performed (DSC, TGA, XRD and IR, DVS).

The HCl salt is a crystalline product based on the XRD result. The IR spectrum shows the presence of characteristic bands of hydro halide salt, the product is solvated. The DSC curve shows the melting with decomposition of the product at 236.4° C. An extra endothermic signal is observed at 72.8° C. due to solvent evaporation. The HCl salt is a hygroscopic product, which when dried (1 h at 25° C. under dry nitrogen flow) adsorbs up to 11.4% water depending on the atmospheric humidity.

The mesylate salt is a crystalline product based on the XRD result. The IR spectrum shows the presence of characteristic bands of sulfonic acid salt. The DSC curve shows the melting with decomposition of the product at 239.0° C. The mesylate salt is a hygroscopic product, which when dried (1 h at 25° C. under dry nitrogen flow) adsorbs up to 4.5% water at high relative humidity.

The HBr salt is a crystalline product based on the XRD result. The IR spectrum shows the presence of characteristic bands of hydro halide salt, the product is solvated. The DSC curve shows the melting with decomposition of the product at 246.6° C. An extra endothermic signal is observed at 97.8° C. due to solvent evaporation. The HBr salt is a hygroscopic product, which when dried (1 h at 25° C. under dry nitrogen flow) adsorbs up to 11.4% water depending on the atmospheric humidity.

The tosylate salt is a crystalline product based on the XRD result. The IR spectrum shows the presence of characteristic bands of sulfonic acid salt. The DSC curve shows the melting of the product at 225.4° C. The tosylate salt is a non-hygroscopic product adsorbing when dried (1 h at 25° C. under dry nitrogen flow) only up to 0.2% water depending on atmospheric humidity.

The esylate salt is a crystalline product based on the XRD result. The IR spectrum shows the presence of characteristic bands of sulfonic acid salt. The DSC curve shows the melting of the product at 217.3° C. The esylate salt is a hygroscopic product, which when dried (1 h at 25° C. under dry nitrogen flow) adsorbs up to 34% water at high relative humidity.

Example 10

Water Solubility of Salts of Compound (I)

An excess of different salts of compound (I) was agitated with water during 24 hours at 20° C. Following filtration, the concentration of compound (I) in the solution was determined by UV spectrometry. The results are summarised in Table 14.

TABLE 14

| Salt of compound (I) | Measured pH | Solubility (g/100 ml $H_2O$) |
|---|---|---|
| with HBr | pH = 1.8 | 0.083 |
| with HCl | pH = 1.8 | 0.038 |
| methanesulphonate (mesylate) | pH = 1.9 | 0.047 |
| ethanesulphonate (esylate) | pH = 2.1 | 0.025 |
| p-toluenesulphonate (tosylate) | pH = 2.1 | 0.023 |

Example 11

Absorption and Plasma Kinetics after Administration of Salts of Compound (I) to Rat Five male SD rats (225±11 g) were used per salt form. From each rat a complete plasma concentration time profile was obtained. Tap water and food were available ad libitum. The test involved salts of compound (I) with HBr, HCl, methanesulphonic acid (mesylate), ethanesulphonic acid (esylate) or p-toluenesulphonic acid (tosylate). The individual salts were dispersed in a 0.5% methocel suspension to a final concentration of 1 mg base eq./ml. The formulations were stored at room temperature.

Administration was oral by gastric intubation: 10 ml/kg to obtain a dose of 10 mg base eq./kg.

Blood samples were collected 30 min, 1, 2, 4, 7 and 24 h after dose administration.

Blood was collected by multiple sampling from a tail vein into Multivette® 600 K3E tubes (Sarstedt). Samples were placed immediately on melting ice and plasma was obtained following centrifugation at 4° C. for 10 minutes at approximately 1900×g. All samples were shielded from daylight and stored at ≤−18° C. prior to analysis.

Plasma samples were analysed for compound (I) using a qualified research LC-MS/MS method (the lower limit of quantification (LLOQ) was 1.00 or 5.00 ng/ml). A limited pharmacokinetic analysis was performed using WinNonlin™ Professional (Version 5.1). A non-compartmental analysis using the lin/log trapezoidal rule with lin/log interpolation was used for all data. An overview of the individual and mean plasma concentrations and some basic pharmacokinetic parameters can be found in Table 15.

TABLE 15

| Time (hours) | HCl salt Mean ± SD | mesylate salt Mean ± SD | HBr salt Mean ± SD | tosylate salt Mean ± SD | esylate salt Mean ± SD |
|---|---|---|---|---|---|
| 0.5 | 3094 ± 235 | 2248 ± 658 | 2852 ± 413 | 2193 ± 1031 | 3054 ± 1069 |
| 1 | 4210 ± 685 | 2964 ± 815 | 3704 ± 524 | 2998 ± 1349 | 4182 ± 1440 |
| 2 | 4292 ± 803 | 2980 ± 611 | 4272 ± 972 | 3274 ± 995 | 4060 ± 1167 |
| 4 | 2710 ± 706 | 2228 ± 592 | 3168 ± 1114 | 2512 ± 960 | 2596 ± 933 |
| 7 | 1942 ± 702 | 1510 ± 372 | 2208 ± 812 | 1625 ± 537 | 1443 ± 603 |
| 24 | 56.1 ± 16.6 | 59.6 ± 27.5 | 53.1 ± 17.1 | 47.9 ± 24.0 | 38.8 ± 16.1 |
| $T_{max}$ (h) | 1.6 ± 0.5 | 1.2 ± 0.4 | 1.8 ± 0.4 | 2.0 ± 1.2 | 1.6 ± 0.5 |
| $C_{max}$ (ng/ml) | 4434 ± 683 | 3056 ± 685 | 4330 ± 867 | 3380 ± 944 | 4400 ± 1377 |
| $t_{1/2\ (4-24\ h)}$ (h) | 3.5 ± 0.3 | 3.7 ± 0.6 | 3.4 ± 0.6 | 3.4 ± 0.6 | 3.3 ± 0.4 |
| $AUC_{0-24\ h}$ (ng·h/ml) | 29624 ± 7215 | 23033 ± 4954 | 31247 ± 7362 | 24307 ± 7457 | 25640 ± 8540 |
| $AUC_{0-inf}$ (ng·h/ml) | 29911 ± 7256 | 23373 ± 5006 | 31517 ± 7269 | 24558 ± 7503 | 25768 ± 8490 |

Example 12

A Route to Prepare Compound (I)

6-{difluoro[6-(1-methyl-1H-pyrazol-4-yl)[1,2,4]-triazolo[4,3-b]pyridazin-3-yl]methyl}quinoline

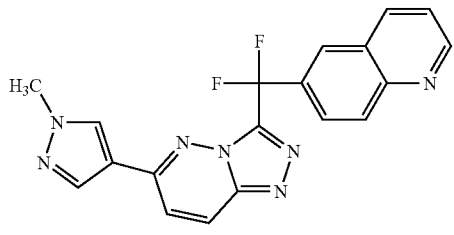 [SMILES: Cn1cc(-c2ccc3nnc(C(F)(F)c4ccc5ncccc5c4)n3n2)cn1]

Step 1: 6-iodoquinoline

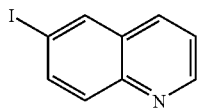

6-bromoquinoline (80.1 g, 0.385 mol) is dissolved in n-butanol (0.8 L). Copper catalyst CuI (3.7 g, 0.019 mol), a copper-ligand N,N'-dimethylethylenediamine (3.4 g, 0.0385 mol) and an iodide source NaI (115.5 g, 0.770 mol) are added and the mixture is heated in a heating jacket, under inert atmosphere to 120° C. After work-up (0.8 L water is added to the reaction mixture, the organic layer is separated off and evaporated) and purification (the crude evaporation residue was crystallized from 150 mL diisopropylether), 6-iodoquinoline was obtained in 80% yield.

1H NMR (600 MHz, CHLOROFORM-d) δ ppm 7.39 (dd, J=8.31, 4.15 Hz, 1 H) 7.83 (d, J=9.06 Hz, 1 H) 7.86-7.96 (m, 1 H) 8.02 (d, J=8.31 Hz, 1 H) 8.19 (s, 1 H) 8.91 (s, 1 H)

Step 2: ethyl oxo(quinolin-6-yl)acetate

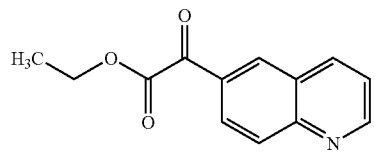 [SMILES: CCOC(=O)C(=O)c1ccc2ncccc2c1]

Under inert atmosphere 255 g 6-iodoquinoline (1 mol) is dissolved in THF and cooled to −20° C. and 808 g IpMgCl·LiCl (1.1 moles) is added. This cold solution is added to a solution of 438 g diethyloxalate (3 moles) in 1800 mL THF at low temperature (−78° C.). The reaction mixture is heated to 0° C. and is quenched with a saturated ammonium acetate solution (0.8 L/mole). Ethyl oxo(quinolin-6-yl)acetate is extracted with ethyl acetate (1 L) from this mixture. After chromatography (silica, heptanes/ethyl acetate) ethyl oxo(quinolin-6-yl)acetate was obtained in 70% yield.

1H NMR (600 MHz, CHLOROFORM-d) δ ppm 1.47 (t, J=7.18 Hz, 3 H) 4.52 (q, J=7.18 Hz, 2 H) 7.52 (dd, J=8.31, 4.15 Hz, 1 H) 8.20 (d, J=8.69 Hz, 1 H) 8.29 (dd, J=8.69, 1.89 Hz, 1 H) 8.30 (dd, J=8.12, 1.32 Hz, 1 H) 8.59 (d, J=1.89 Hz, 1 H) 9.05 (dd, J=4.34, 1.70 Hz, 1 H)

Step 3: ethyl 2,2-difluoro(quinolin-6-yl)acetate

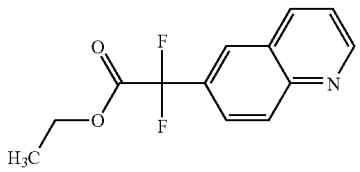 [SMILES: CCOC(=O)C(F)(F)c1ccc2ncccc2c1]

A suitable autoclave reactor was loaded with 170 g (0.74 mol) ethyl oxo(quinolin-6-yl)acetate and 1.3 L dichloromethane. Then 26 g HF (1.3 mol) and 400 g SF4 (3.7 mol) were condensed from gas bottles into the reactor. The mixture was heated at 60° C. for 24 h. After cooling to ambient temperature, the mixture was quenched with water and neutralized by addition of NaHCO$_3$. After separation of the organic layer and evaporation, the residue was chromatographed affording 138 g ethyl difluoro(quinolin-6-yl)acetate (yield is 74%).

1H NMR (400 MHz, CHLOROFORM-d) δ ppm 1.30 (t, J=7.05 Hz, 3 H) 4.33 (q, J=7.30 Hz, 2 H) 7.45 (dd, J=8.31, 4.28 Hz, 1 H) 7.91 (dd, J=8.81, 2.01 Hz, 1 H) 8.11-8.14 (m, 1 H) 8.19 (d, J=8.81 Hz, 1 H) 8.21 (dd, J=7.55, 1.26 Hz, 1 H) 8.98 (dd, J=4.03, 1.51 Hz, 1 H)

Step 4: 2,2-difluoro-2-quinolin-6-ylacetohydrazide

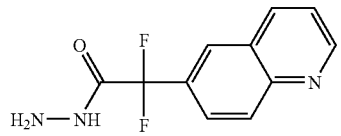 [SMILES: NNC(=O)C(F)(F)c1ccc2ncccc2c1]

To a reactor under inert atmosphere was added 31.05 mL 2-methyl-2-butanol and 12.58 mL (0.259 mol) hydrazine hydrate. Then a solution of 26 g (0.103 mol) ethyl difluoro (quinolin-6-yl)acetate in 125 mL 2-methyl-2-butanol was dosed to the hydrazine solution at room temperature. The precipitate was filtered off from the reaction mixture and was washed with water and dried at 50° C. 22.51 g 2,2-difluoro-2-quinolin-6-ylacetohydrazide was obtained in 90% yield.

1H NMR (400 MHz, DMSO-d$_6$) δ ppm 4.77 (br. s., 2 H) 7.65 (dd, J=8.31, 4.28 Hz, 1 H) 7.92 (dd, J=8.81, 2.01 Hz, 1 H) 8.18 (d, J=8.81 Hz, 1 H) 8.28-8.33 (m, 1 H) 8.56 (d, J=8.31 Hz, 1 H) 9.00-9.06 (m, 1 H) 10.18 (br. s., 1 H)

Step 5: 3-chloro-6-(1-methyl-1H-pyrazol-4-yl)pyridazine

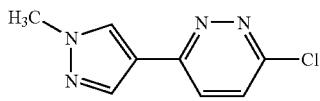

Water (253 mL) and THF (842 mL) were put in the reaction balloon. The reagents were added one by one to the stirred reaction mixture: potassium phosphate monohydrate 86.2 g (374 mmol) and BTEAC 2.25 g (9.88 mmol). Then 3-chloro-6-iodopyridazine, 45 g (187.2 mmol) and 1-methyl-4-(4,4,5,5-tetramethyl-[1,3,2]dioxaborolan-2-yl)-1H-pyrazole, 46.73 g (224.6 mmol) were added and finally triphenylphosphine, 1.96 g (7.49 mmol) and palladiumdiacetate, 420 mg (1.87 mmol) were added. The reaction mixture was heated at 65° C. for 16 h. The reaction mixture was allowed to cool to 60° C. Then 935 mL water and 301.5 g sodium chloride were added. The mixture was stirred for 15 minutes and allowed to cool to 45° C. The phases were separated and the organic layer was washed with a solution of 45 g sodium chloride in 374 mL water. The organic layer was separated and stirred with magnesium sulphate (225 g) and charcoal (4.5 g). The mixture was filtered and evaporated. The evaporation residue was co-evaporated with toluene twice and evaporated further till a final volume of 200 ml. This residue was stirred for 16 h at room temperature. The resulting solids were collected by filtration. The solids were dried at reduced pressure affording 29.7 g of the title compound (152.6 mmol, yield 82%).

1H NMR (600 MHz, CHLOROFORM-d) δ ppm 4.00 (s, 3 H) 7.46 (d, J=8.69 Hz, 1 H) 7.56 (d, J=9.06 Hz, 1 H) 7.98 (s, 1 H) 8.11 (s, 1 H)

Step 6: 6-{difluoro[6-(1-methyl-1H-pyrazol-4-yl)[1,2,4]triazolo[4,3-b]pyridazin-3-yl]methyl}quinoline

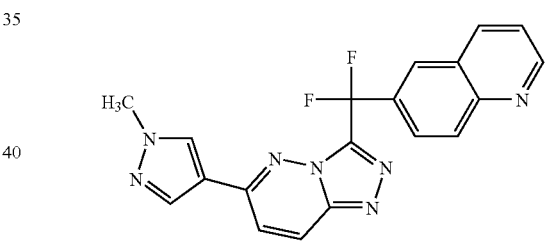

To a reactor under inert atmosphere was added 73.84 g (0.38 mol) 3-chloro-6-(1-methyl-1H-pyrazol-4-yl)pyridazine, 90 g (0.38 mol) 2,2-difluoro-2-quinolin-6-ylacetohydrazide and 1200 mL 1-methoxy-2-propanol. Then 29.85 mL (0.455 mol) methane sulphonic acid was added and the reaction mixture was heated at 80° C. for 8 hours. After cooling to ambient temperature the mesylate salt of the title compound was filtered off from the reaction mixture. This salt was dissolved in a mixture of 400 mL ethanol and 300 mL water, after alkalisation at 80° C. with 50 mL ammonia (0.65 mol) in 200 mL water the free base of the title compound precipitates and was filtered off. This precipitate was dried at 50° C. and was subsequently re-crystallized from 2-propanol (1.8 L/mol) to yield the title compound in 75% yield.

1H NMR (600 MHz, CHLOROFORM-d) δ ppm 4.01 (s, 3 H) 7.40 (d, J=9.44 Hz, 1 H) 7.50 (dd, J=8.31, 4.15 Hz, 1 H) 7.95 (s, 1 H) 7.98 (s, 1 H) 8.08 (dd, J=8.69, 1.89 Hz, 1 H) 8.14 (d, J=9.82 Hz, 1 H) 8.25 (d, J=9.06 Hz, 1 H) 8.27 (dd, J=8.31, 1.51 Hz, 1 H) 8.29 (d, J=1.13 Hz, 1 H) 9.02 (dd, J=4.15, 1.89 Hz, 1 H)

Example 13

A Route to Prepare Compound (I)

6-{difluoro[6-(1-methyl-1H-pyrazol-4-yl)[1,2,4]-triazolo[4,3-b]pyridazin-3-yl]methyl}quinoline

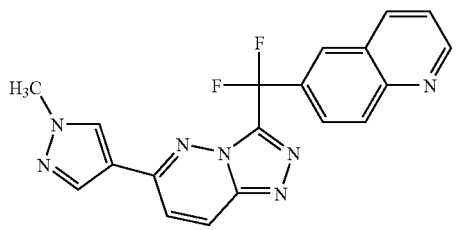 [SMILES: Cn1cc(-c2ccc3nnc(C(F)(F)c4ccc5ncccc5c4)n3n2)cn1]

Step 1: tert-butyl 2-[6-(1-methyl-1H-pyrazol-4-yl)pyridazin-3-yl]hydrazinecarboxylate

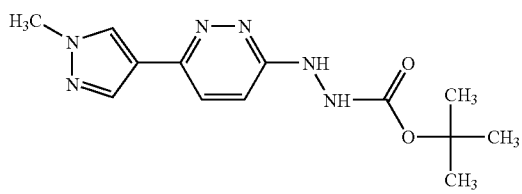 [SMILES: Cn1cc(-c2ccc(NNC(=O)OC(C)(C)C)nn2)cn1]

tert-butyl carbazate, 8.98 g (67.3 mmol) and 3-chloro-6-(1-methyl-1H-pyrazol-4-yl)pyridazine (11.9 g, 61.1 mmol) were mixed in 1-butanol (245 mL). This mixture was heated till 90° C. and stirred at that temperature for 16 h. The reaction mixture was cooled and water (250 mL) and ethylacetate (250 mL) were added. The biphasic mixture was neutralised with sodium hydrogencarbonate till the pH is 7. Then the organic layer was separated and the water layer was extracted with ethylacetate (250 mL). The combined organic layers were washed once with water (250 mL) and evaporated. The residue was stirred in isopropylether, filtered off and dried under vacuum. Yield: 5.9 g (20.3 mmol; 33%) of the title compound.

Step 2: sodium 2,2-difluoro(quinolin-6-yl)acetate

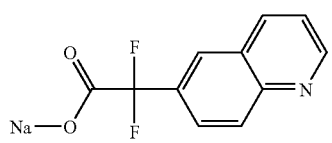

8.1 g (32.2 mmol) of ethyl difluoro(quinolin-6-yl)acetate was added to a reaction balloon. Methanol (40.5 mL) and water (2.9 mL) were added. To this solution, 1.29 g sodium hydroxide (32.2 mmol) was added at room temperature for 16 h. The resulting solids were filtered off and dried under vacuum. Yield 4.5 g (18.4 mmol; 57%).

Step 3: 6-{1,1-difluoro-2-[(6E)-6-hydrazono-3-(1-methyl-1H-pyrazol-4-yl)pyridazin-1(6H)-yl]-2-oxoethyl}quinoline

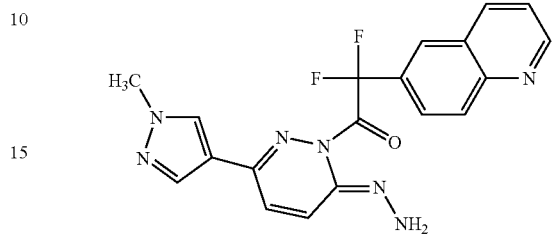

900 mg (3.67 mmol) of sodium difluoro(quinolin-6-yl)acetate was dissolved in acetonitrile (27 mL). 1.17 g (4.04 mmol) of tert-butyl 2-[6-(1-methyl-1H-pyrazol-4-yl)pyridazin-3-yl]hydrazinecarboxylate was added and 300 mg (4.41 mmol) of 1H-imidazole was added at once. 0.561 mL (7.71 mmol) of thionyl chloride was added over 5 minutes at room temperature. The mixture was stirred for 2 hours at room temperature, giving tert-butyl (2E)-2-{2-[difluoro(quinolin-6-yl)acetyl]-6-(1-methyl-1H-pyrazol-4-yl)pyridazin-3(2H)-ylidene}hydrazinecarboxylate. Then, 0.722 mL (11.0 mmol) of methanesulphonic acid was added at room temperature and stirred for 16 h. The resulting solids were filtered off under argon atmosphere, yielding 6-{1,1-difluoro-2-[(6E)-6-hydrazono-3-(1-methyl-1H-pyrazol-4-yl)pyridazin-1(6H)-yl]-2-oxoethyl}quinoline and used as such in the next step.

Step 4: 6-{difluoro[6-(1-methyl-1H-pyrazol-4-yl)[1,2,4]-triazolo[4,3-b]pyridazin-3-yl]methyl}quinoline (compound (I))

The crude 6-{1,1-difluoro-2-[(6E)-6-hydrazono-3-(1-methyl-1H-pyrazol-4-yl)pyridazin-1(6H)-yl]-2-oxoethyl}quinoline from step 3 above (3.67 mmol) was brought in a reaction balloon under argon. 36 mL of 1-methoxy-2-propanol was added and the mixture was stirred at 105° C. for 1 h. Then the reaction mixture was brought to gentle reflux for one additional hour (108° C.). The reaction mixture was allowed to cool to room temperature and poured out in a solution of 10 g of sodium carbonate in 100 mL of water. 100 mL toluene was added and the layers were separated. The water layer was extracted with toluene (100 mL). The combined organic layers were washed with water and evaporated, yielding 700 mg of compound (I) (1.86 mmol; 51%).

Example 14 c-Met Inhibitory Activity of Compound of Formula (I)

Cloning, Expression, and Purification of Recombinant c-Met Protein

This example describes the cloning, expression, and purification of the cytoplasmic domain of c-Met which has the c-Met receptor tyrosine kinase activity. The cytoplasmic domain has 435 amino acids and shows high homology with the SRC family of tyrosine kinases (Park et al., 1987, Proc Natl Acad Sci USA. 84(18):6379-83). The c-Met cytoplasmic domain as prepared herein may be used for in vitro assays of the c-Met kinase activity, and the effect of agents of the invention thereon.

A cDNA for the cytoplasmic domain of Met receptor, containing the tyrosine kinase domain, was amplified by PCR. Oligonucleotides were custom synthesized by Gibco-BRL (Carlsbad, Calif.). Forward oligonucleotide metkinF2 is identical to nucleotides 3068-3097 of the nucleotide sequence listed in NM_000245, except that nucleotides between 3073 and 3078 have been altered to create a BamHI site for cloning purposes. Reverse oligonucleotide metkinR2a is identical to nucleotides 4378-4348 of the complementary sequence of that listed in NM_000245 except that nucleotides between 4372-4367 have been altered to create a XhoI site (underlined) for cloning purposes. The oligonucleotides were used as PCR primers to amplify Met receptor cytoplasmic domain cDNA from Quick Clone placental cDNA (Clontech; 25 Palo Alto, Calif.). Amplification was performed using Taq DNA polymerase (Gibco-BRL; Carlsbad, Calif.), 1.25 mM each dNTP, 200 nM each oligo, in a 50 µl volume. The thermocycle profile was 30 cycles of each containing 94° C. for 30 seconds, 60° C. for 30 seconds, and 72° C. for 1 minute, on a Perkin Elmer 9600 thermocycler.

The amplified cDNA for the cytoplasmic domain of Met receptor was cloned onto an expression vector. The PCR product was digested with BamHI (New England Biolabs; Beverly, Mass.) and XhoI (New England Biolabs). A digested 1.3 kb product was isolated and purified from a 1% agarose gel using Gene Clean (Qbiogene; Irvine, Calif.). Vector pFastBacHTa (Gibco-BRL) was digested with BamHI and XhoI (New England Biolabs) and the 4.7 kb linear fragment was purified from a 1% agarose gel using Gene Clean (Bio101). The 1.3 kb Met cDNA fragment was ligated to pFastBacHTa vector at 4° C. for 16 hours with T4 DNA ligase (New England Biolabs) in a final volume of 10 µl. Cloning the Met cytoplasmic domain cDNA clone into the BamHI site of pFastBacHTa placed the cDNA in-frame with the His-6 tag of the vector to allow for expression of an N-terminal His-tagged protein. Half the ligation mix (5 µL) was used to transform 50 µl DH5α competent *E. coli* cells (Gibco-BRL). The transformation mix was plated onto LB agarose plates containing 100 µg/ml ampicillin and incubated for 16 hours at 37° C. Colonies were picked from these plates and grown in LB broth containing 100 µg/ml ampicillin for 16 hours. Plasmid DNA was isolated using Qiagen plasmid DNA purification reagents (Qiagen; Valencia, Calif.) and clones screened by digest with BamHI/XhoI. Three clones which had the appropriate size fragment released from the digest were submitted to ACGT, Inc for DNA sequence analysis.

One clone, pFastBacHTmetkin-15, contained no mutations in the cloned c-Met cytoplasmic domain and was used to generate a recombinant baculovirus for expression. Recombinant baculovirus was generated using the Gibco BRL Bac-To-Bac system following the protocol specified by the manufacturer. Briefly, DH10Bac cells were transformed with pFastBacHTmetkin-15, clones were selected, viral DNA isolated, and screened by PCR for Met cDNA insert. Sf9 insect cells were transfected with the recombinant baculovirus DNA. Media containing P0 viral stock 25 was collected and used for 2 subsequent rounds of viral amplification.

Multiple concentrations of amplified viral stock were used to infect Sf9 cells. Cells were harvested 24, 48, and 72 hours post transfection. Infected Sf9 cells were lysed in 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin and total protein concentration determined in a BCA assay (Pierce; Rockford, Ill.). Cell lysates were separated on a 4-15% SDS-PAGE then transferred to nitrocellulose membrane for immunoblot analysis. Nitocellulose blots were probed with an anti-His6 antibody to confirm expression of the His-tagged met kinase protein. Optimal viral concentration to Sf9 cell ratio was determined by examination of lysates collected from different infection conditions. Maximal protein recovery occurred 48 hours post infection.

A small-scale expression/purification of the His-tagged cytoplasmic domain of Met receptor was performed. Sf9 insect cells transfected with the recombinant baculovirus that expresses the His-tagged cytoplasmic domain of Met receptor were lysed in buffer containing 50 mM Tris-HCl pH 8.0, 150 mM NaCl, 150 mM imidazole, 1.0 mM PMSF, 0.5% NP40, 3.5 µg/ml leupeptin, 3.5 µg/ml aprotinin. The lysate was incubated with 5 ml of a 50% solution of Ni-agarose beads (Qiagen) in PBS for 2 hours rotating at 4° C. to capture the His-tagged protein. The lysate containing His-tagged protein bound to Ni-agarose beads was loaded onto a 10 ml column. Ni-agarose beads were allowed to pack and supernatant allowed to flow through. The packed column was then washed with 60 ml of wash buffer (same as lysis buffer). 5 ml of elution buffer (50 mM Tris-HCl pH 8, 150 mM NaCl, 150 mM imidazole, 1.0 mM PMSF) was added to the column and 10 fractions (0.5 ml volume each) were collected. Small aliquots of each fraction were separated by 4-15% SDS-PAGE and either transferred to nitrocellulose for immunoblot analysis or processed for Coomassie stain (Bio-Safe Safe Coomassie, Bio-Rad). The major protein band on the Coomassie stain gel has the appropriate size for His6-MetKin (52 kD), corresponding to the His-tagged protein detected by immunoblot. Protein concentration as estimated from the Coomassie stain gel was approximately 2 mg/ml.

Recombinant viral stock was transferred to the contract lab, Pan Vera (Madison, Wis.) for large-scale expression and purification of His6-MetKin in quantities sufficient for High Throughput Screening. A 60 L scale up and 4 step purification scheme yielded 98.4 mg of protein that is more than 95% pure.

Effect of Compound (I) on the Autophosphorylation of the c-Met Kinase

The present autophosphorylation assay uses radioactive ATP to measure the incorporation of phosphate upon c-Met autophosphorylation. The assay procedure for screening is as follows.

Materials c-Met enzyme (purchased from Panvera, Lot 40047X, 2.4 mg/ml); "Assay buffer" (13.3 mM MOPS pH 7; 0.33 mM EDTA); "Enzyme buffer" (20 mM MOPS pH 7; 1 mM EDTA; 0.01% Brij 35; 5% glycerol; 0.1% beta mercapto-EtOH); 100 mM MgAc; 3% phosphoric acid; 75 mM phosphoric acid; 1 mM ATP-stock; [$^{33}$P]-γ-ATP (NEN, NEG602H); round-bottom 96-well plates (Corning, 3799); Filtermat P30-filters (Perkin Elmer); "Enzyme mix" (698.80 µl of Enzyme buffer as above+1.17 µl of c-Met enzyme as above); "Substrate mix" (946.00 µl of 100 mM MgAc+50.00 µl ATP (0.1 mM)+4.00 µl [$^{33}$P]-γ-ATP as above).

Protocol Steps

1. Distribute 15 µl assay buffer per well.
2. Add 0.5 µl dilution of tested c-Met inhibitor (e.g., compound (I) or its forms or salts) in DMSO.
3. Add 5 µl Enzyme mix per well (control: Enzyme buffer in blanc).
4. Add 5 µl Substrate mix per well.
5. Incubate at room temperature for 60 min.
6. Stop reaction with 3% phosphoric acid, 5 µl per well
7. Shake plate
8. Spot 5 µl from a well to filtermat P30.

9. Wash filter 3× for 5 min in 75 mM phosphoric acid.
10. Wash filter 1× for 2 min in methanol.
11. Dry filter for 1 hour at 60° C.
12. Expose the filter to phosphor storage cassette overnight on low energy phosphor storage plate, and detect and quantify the signal using a suitable phosphorimager (herein, Typhoon)

Results

Using the above detailed assay, $IC_{50}$ values for c-Met kinase inhibition have been determined as approximately $7.01 \times 10^{-9}$ M and $1.32 \times 10^{-8}$ M for the free base form of compound (I) and for the salt of compound (I) with HCl, respectively.

Example 15

Biological Activity of Compound of Formula (I)

U87MG Glioblastoma Tumour Xenograft Model
Introduction

The U87MG glioblastoma cell line (Piedmont Research Center LLC) expresses the c-Met receptor and responds to Human Growth Factor (HGF). This study investigated whether treatment with an inhibitor of c-Met is efficacious against the U87MG glioblastoma tumor xenograft model. This study utilized a tumor growth inhibition (TGI) assay to test per os (p.o.) compound monotherapy in groups of fifteen nude mice. A control group was treated with vehicle, 20% Hydroxypropyl Beta-Cyclodextrin (HPBCD). All treatments began on Day 1 (D1) in mice bearing established subcutaneous (s.c.) U87MG tumors.

Methods and Materials
Mice

Female athymic nude mice (Harlan) were 10-11 weeks old with a BW range of 18.1-25.0 g on D1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® bed-o-cobs® Laboratory Animal Bedding in static microisolators on a 12-hour light cycle at 21-22° C. (70-72° F.) and 40-60% humidity. All animals were housed in a Laboratory Animal Medicine facility that is fully accredited by the American Association for Assessment and Accreditation of Laboratory Animal Care (AAALAC). All procedures involving animals were conducted in compliance with the NIH *Guide for the Care and Use of Laboratory Animals* and all protocols were approved by an Internal Animal Care and Use Committee (IACUC).

Tumor Implantation

Xenografts were initiated from U87MG human glioblastoma tumor fragments maintained by serial transplantation in athymic nude mice. Each test mouse received a subcutaneous U87MG tumor fragment (1 mm³) implanted in the right flank, and the growth of tumors was monitored as the average size approached 200 mm³. Twelve days later, on Day 1 of the study, the animals were sorted into 4 groups (n=12-15 mice/group) with individual tumor volumes ranging from 172-352 mm³ and group mean tumor volumes of 216 mm³. Tumor volume was calculated using the formula:

$$\text{Tumor Volume} = \frac{w^2 \times l}{2}$$

where w=width and l=length in mm of the tumor. Tumor weight may be estimated with the assumption that 1 mg is equivalent to 1 mm³ of tumor volume.

Drug Treatment

Dosing solutions of compounds of the present invention were prepared fresh weekly in a vehicle consisting of 20% Hydroxypropyl Beta-Cyclodextrin (HPBCD) in water. In all groups, the dosing volume of 0.2 mL/20-g mouse was scaled to the body weight of each animal. Doses were given to allow for the HCl salt form of the compound.

Tumor Growth Inhibition (TGI) Analysis

TGI was calculated from the difference between the median tumor volumes of vehicle-treated and drug-treated mice, expressed as a percentage of the median tumor volume of the vehicle-treated control group, by the following relation:

$$\% \ TGI = \left( \frac{\text{Median Tumor } Volume_{control} - \text{Median Tumor } Volume_{drug\text{-}treated}}{\text{Median Tumor } Volume_{control}} \right) \times 100$$

The MTV (n) is defined as the median tumor volume (MTV) for the number of animals, n, remaining in the study on that day.

Toxicity

Animals were weighed daily for the first five days of the study and then twice weekly. The mice were examined frequently for overt signs of any adverse, drug-related side effects, and clinical signs of toxicity were recorded when observed. Acceptable toxicity is defined as a group mean body-weight (BW) loss of less than 20% during the study, and not more than one treatment-related (TR) death among ten animals. A death is classified as TR if it is attributable to treatment side effects as evidenced by clinical signs and/or necropsy, or due to unknown causes during the dosing period or within 10 days of the last dose. A death is classified as non treatment-related (NTR) if there is no evidence that the death was related to drug side effects. A death is classified as non treatment-related unknown (NTRu) if the cause of death is unknown.

Statistical and Graphical Analyses

The Mann-Whitney U-test, for analysis of medians, was used to determine the statistical significance of the difference between the MTVs. Prism 3.03 (GraphPad) for Windows was used for the statistical analyses and graphic presentations. Tumor growth was plotted as the median tumor volume, versus time, for each group in the study. In addition, final tumor volume and final percent tumor growth inhibition (% TGI) were also represented on the graph or on a separate bar graph. (*=p≤0.05, =p≤0.01, *=p≤0.001). Results of the U87MG tumor growth study are shown in FIG. 10 and FIG. 11.

Figure 10:
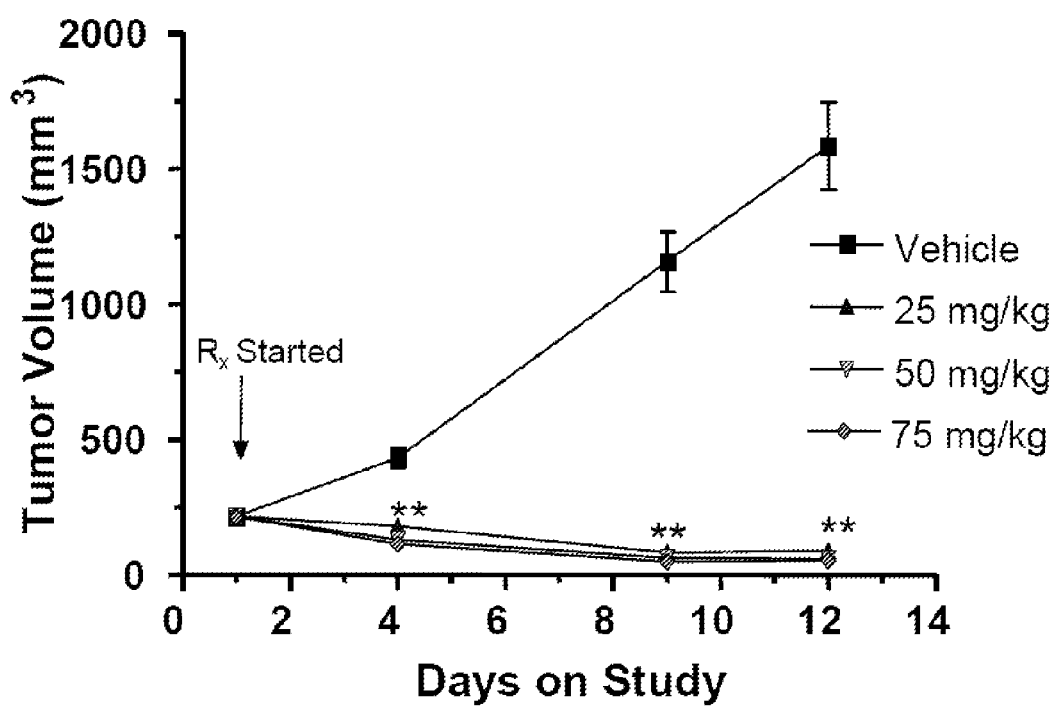
FIG. 10 illustrates the effect of compound (I) on U87MG tumor growth inhibition.

FIG. 10: Compound (I) was administered p.o. at doses of 25, 50, and 75 mg/kg. All doses produced statistically significant, tumor growth inhibition of U87MG tumors grown subcutaneously in athymic nude mice (p<0.01). Tumor regression was also observed with all three doses. The 25 mg/kg dose was administered once a day (q.d.) on day 1 and b.i.d. to day 12. The 50 mg/kg dose was administered b.i.d. for 7 days, with a 24-hr pause, then q.d. to day 12. Like the 50 mg/kg dose, the 75 mg/kg dose was administered b.i.d. for 7 days, with a 24-hr pause, then q.d. to day 12.

Figure 11:
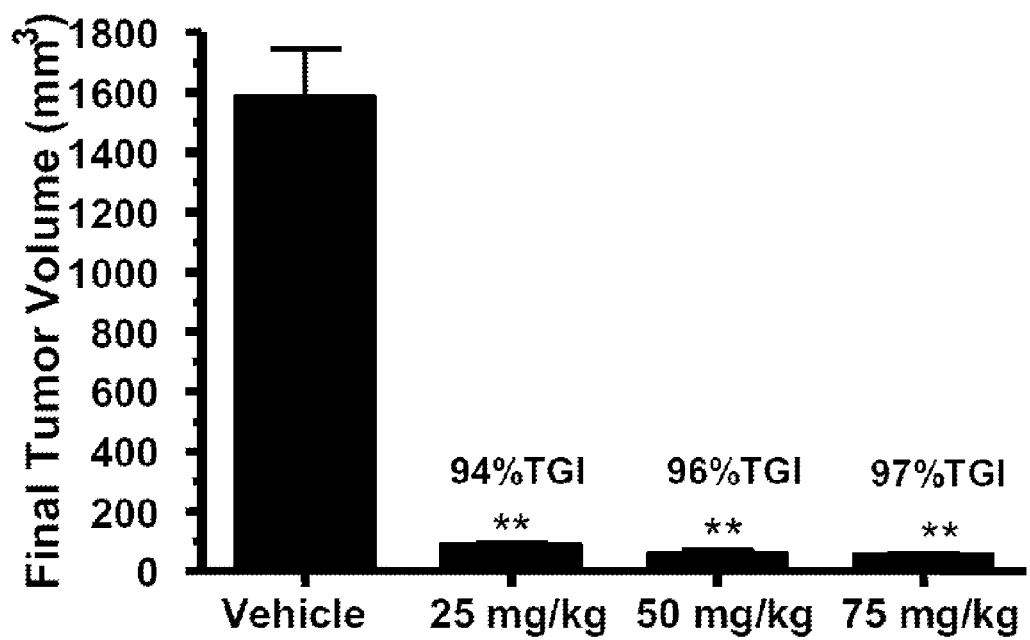
FIG. 11 illustrates the effect of compound (I) on U87MG final tumor volume.

FIG. 11: Compound (I) was administered p.o. at doses of 25, 50, and 75 mg/kg. On the last day of treatment (Day 12), mean tumor volume was decreased by 94% (p<0.01), 96% (p<0.01) and 97% (p<0.01) at doses of 25, 50, and 75 mg/kg, respectively. The 25 mg/kg dose was administered once a day (q.d.) on day 1 and b.i.d. to day 12. The 50 mg/kg dose was administered b.i.d. for 7 days, with a 24-hr pause, then q.d. to day 12. Like the 50 mg/kg dose, the 75 mg/kg dose was administered b.i.d. for 7 days, with a 24-hr pause, then q.d. to day 12.

S114 Tumor Model

Methods

Mice

Female athymic nude mice (CD-1, nu/nu, 9-10 weeks old) were obtained from Charles River Laboratories (Wilmington, Mass.) and were maintained according to NIH standards. All mice were group housed (5 mice/cage) under clean-room conditions in sterile micro-isolator cages on a 12-hour light/dark cycle in a room maintained at 21-22° C. and 40-50% humidity. Mice were fed irradiated standard rodent diet and water ad libitum. All animals were housed in a Laboratory Animal Medicine facility that is fully accredited by the American Association for Assessment and Accreditation of Laboratory Animal Care (AAALAC). All procedures involving animals were conducted in compliance with the NIH Guide for the Care and Use of Laboratory Animals and all protocols were approved by an Internal Animal Care and Use Committee (IACUC).

S114 Tumors

The murine NIH 3T3 derived cell line S114, which has been engineered to over-express both Human Growth Factor (HGF) and the human c-Met receptor, was propagated in DMEM media (Life Technologies, Bethesda, Md.). Immediately prior to injection, cells were washed counted and resuspended in PBS. Female athymic nude mice weighing no less than 20-21 grams were inoculated subcutaneously in the left inguinal region of the thigh with $5 \times 10^6$ cells in a delivery volume of 0.1 mL. Tumors were allowed to grow to for five days.

Drug Treatment

Mice were dosed orally at 100 mg/kg compound in 20% HPBCD or with vehicle (20% HPBCD, control group). Dosing was continued for 4 consecutive days. Compounds of the invention were prepared fresh daily as a clear solution in 20% HPBCD and administered as described above. Body weight was measured at the end of the study and a loss of body weight >10% was used as an indication of lack of compound tolerability. Unacceptable toxicity was defined as body weight loss >20% during the study. Mice were closely examined daily at each dose for overt clinical signs of adverse, drug-related side effects. No significant change in body weight or behavior was noted in the study.

Analysis

On the day of study termination, a final tumor volume and final body weight were obtained on each animal. Mice were euthanized using 100% $CO_2$ and tumors were immediately excised intact and weighed, with final tumor wet weight (grams) serving as a primary efficacy endpoint. Prism 3.03 (GraphPad) for Windows was used for the statistical analyses and graphic presentations. Results of the S114 tumor study are shown in FIG. 12.

Figure 12:
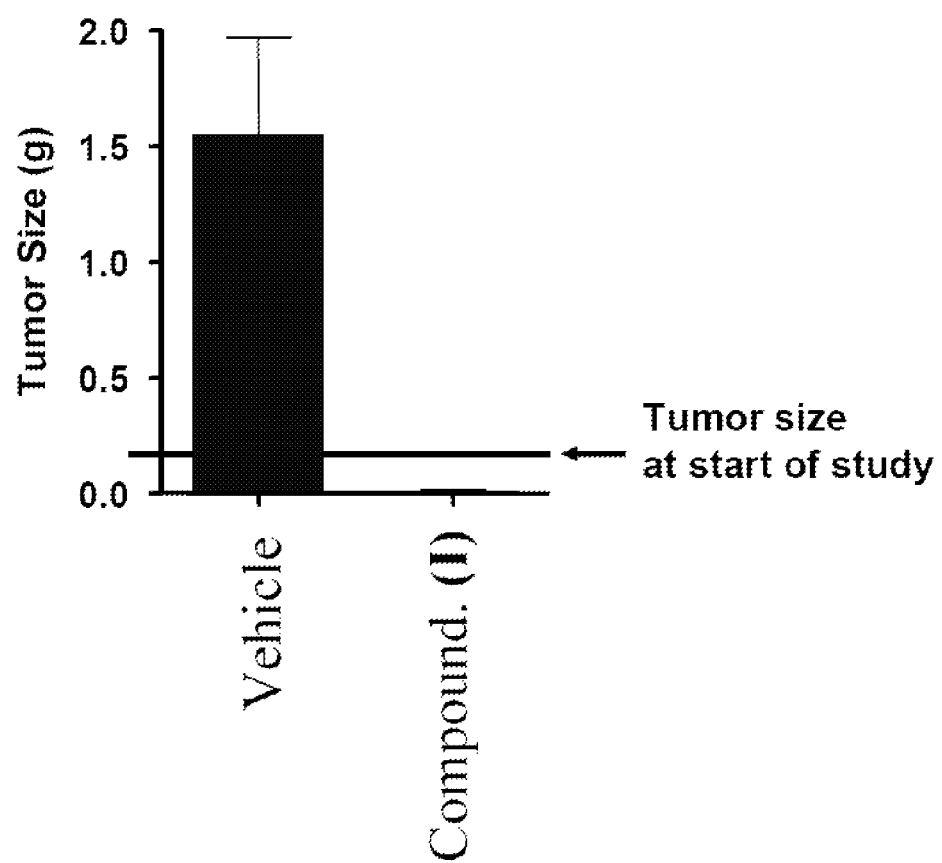
FIG. 12 illustrates the effect of compound (I) on S114 tumor regression.

FIG. 12 and Table 16: Compound (I) was administered p.o. at a dose of 100 mg/kg q.d., for four consecutive days. The S114 tumors regressed in all five mice treated with compound (I). Furthermore, tumors in three of the five mice regressed to non-palpable, non-detectable tumors by the end of the study.

TABLE 16

| Final tumour weights | |
|---|---|
| Vehicle Control | Compound (I) |
| 1.25 g | 0.017 g |
| 2.22 g | 0.017 g |
| 1.44 g | no tumour |
| 1.69 g | no tumour |
| 1.16 g | no tumour |

The invention claimed is:

1. A process for preparing a salt of a compound of formula (I):

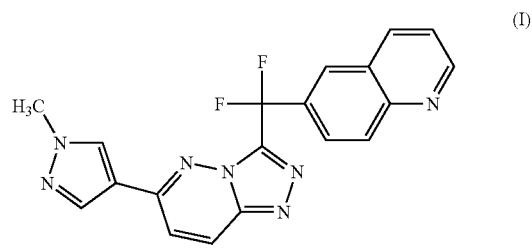 [SMILES: Cn1cc(-c2ccc3nnc(C(F)(F)c4ccc5ncccc5c4)n3n2)cn1]

comprising reacting an intermediate of formula (II)

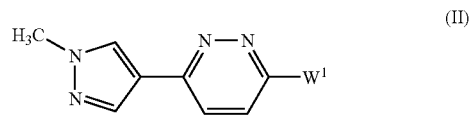

wherein $W^1$ is a leaving group, with an intermediate of formula (III)

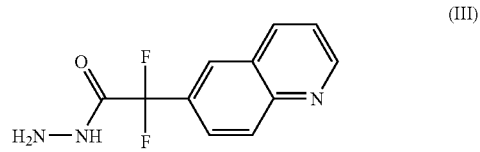

wherein said reacting is in the presence of an acid.

2. A process for preparing the compound of formula (I) comprising:

(a) reacting an intermediate of formula (II)

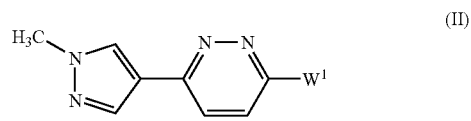

wherein W¹ is a leaving group, with an intermediate of formula (III)

(III)

in the presence of an acid, thereby obtaining a salt of the compound of formula (I); and (b) contacting said salt with a base, thereby obtaining the compound of formula (I).

3. The process of claim 1 or 2, wherein the intermediate of formula (III) is prepared by a process comprising:

(a) converting a Grignard reagent of 6-haloquinoline of formula (VI)

(VI)

wherein X¹ is chloro, bromo or iodo, to an intermediate of formula (VIII)

(VIII)

wherein R¹ is $C_{1-6}$ alkyl;

(b) deoxofluorinating the intermediate of formula (VIII), thereby obtaining an intermediate of formula (IX)

(IX)

and (c) treating the intermediate of formula (IX) with hydrazine or hydrazine equivalent, thereby obtaining the intermediate of formula (III).

4. The process of claim 1 or 2, wherein said acid has pKa less than about 3.

5. The process of claim 4, wherein said acid is chosen from a hydrohalic acid, preferably HCl or HBr, sulphuric acid ($H_2SO_4$), trifluoroacetic acid, or a sulphonic acid, preferably p-toluene sulphonic acid, p-bromobenzene sulphonic acid, trifluoromethane sulphonic acid, camphor sulphonic acid, methane sulphonic acid or ethane sulphonic acid.

6. The process of claim 5, wherein said acid is methane sulphonic acid.

7. A process for preparing a compound of the formula (I)

(I)

comprising:
(a) reacting an intermediate of formula (X)

(X)

wherein PG is a protecting group, with an intermediate of formula (XI)

(XI)

wherein E is —OH, —O$^{(-)}$M$^{(+)}$ or —OR¹, and M is alkali metal and R¹ is $C_{1-6}$ alkyl, thereby obtaining an intermediate of formula (XII)

(XII)

(b) removing the protecting group PG from the intermediate of formula (XII), thereby obtaining an intermediate of formula (XIII)

(XIII)

and (c) converting the intermediate of formula (XIII) to the compound of formula (I).

8. The process of claim 4, wherein said acid has pKa less than about 2.

9. The process of claim 4, wherein said acid has pKa equal or less than 1.

10. A crystalline form of the compound of formula (I)

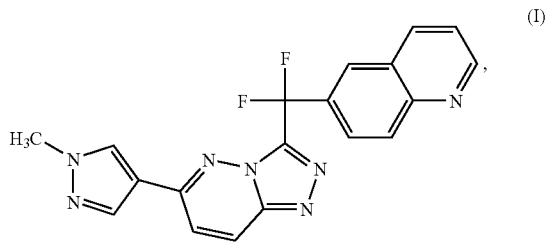 [SMILES: Cn1cc(-c2ccc3nnc(C(F)(F)c4ccc5ncccc5c4)n3n2)cn1]

wherein the crystalline form has any one or more of the following:
- a X-ray powder diffraction (XRPD) pattern comprising peaks at diffraction angles (2θ) of 6.1±0.2, 16.5±0.2, and 19.0±0.2;
- a XRPD pattern comprising peaks at diffraction angles (2) similar to those shown in FIG. 1;
- an IR spectrum comprising peaks at absorption bands (cm$^{-1}$) of 1027±2, 835±2 and 822±2;
- an IR spectrum comprising peaks at absorption bands (cm$^{-1}$) as shown in Table 2 or FIG. 2;
- an IR spectrum comprising peaks at absorption bands (cm$^{-1}$) of 1027±2, 982±2 and 892±2;
- a melting endotherm at between 199.0° C. and 203.5° C., as measured by differential scanning calorimetry (DSC) when scanning at a scan rate of 10° C. per minute.

11. The crystalline form of claim 10, wherein the crystalline form is pure.

12. A crystalline form of the compound of formula (I)

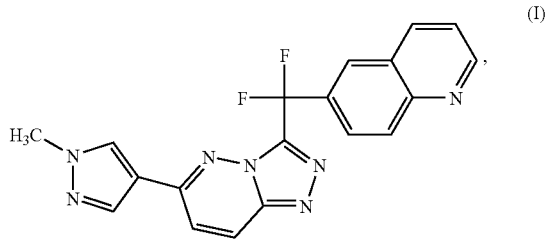 [SMILES: Cn1cc(-c2ccc3nnc(C(F)(F)c4ccc5ncccc5c4)n3n2)cn1]

wherein the crystalline form has any one or more of the following:
- a XRPD pattern comprising peaks at diffraction angles (2θ) of 6.7±0.2, 11.3±0.2, and 15.3±0.2;
- a XRPD pattern comprising peaks at diffraction angles (2θ) essentially the same as shown in FIG. 3;
- an IR spectrum comprising peaks at absorption bands (cm$^{-1}$) of 1576±2, 1225±2, 836±2 and 830±2;
- an IR spectrum comprising peaks at absorption bands (cm$^{-1}$) of 1042±2, 987±2 and 969±2;
- an IR spectrum comprising peaks at absorption bands (cm$^{-1}$) as shown in Table 4 or FIG. 4.

13. The crystalline form of claim 12, wherein the crystalline form is pure.

14. A hydrate form of the compound of the formula (I)

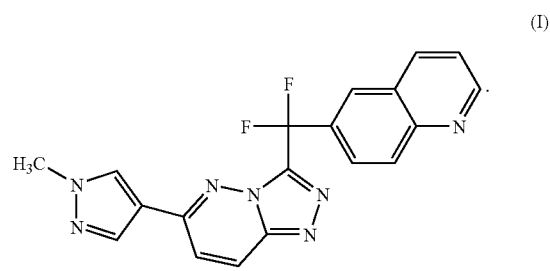 [SMILES: Cn1cc(-c2ccc3nnc(C(F)(F)c4ccc5ncccc5c4)n3n2)cn1]

15. The hydrate form of claim 14, wherein said hydrate form has any one or more of the following:
- a XRPD pattern comprising peaks at diffraction angles (2θ) of 8.4±0.3, 19.5±0.3, and 29.0±0.3;
- a XRPD pattern comprising peaks at diffraction angles (2θ) similar to those shown in FIG. 5;
- an IR spectrum comprising peaks at absorption bands (cm$^{-1}$) of 836±2, 825±2 and 668±2;
- an IR spectrum comprising peaks at absorption bands (cm$^{-1}$) of 3299±2, 985±2 and 668±2;
- an IR spectrum comprising peaks at absorption bands (cm$^{-1}$) as shown in Table 6 or FIG. 6.

16. A solid form of the compound of formula (I) comprising a mixture of at least two forms selected from the crystalline forms as claimed in claim 10, 12 or 14.

17. A salt of the compound of formula (I)

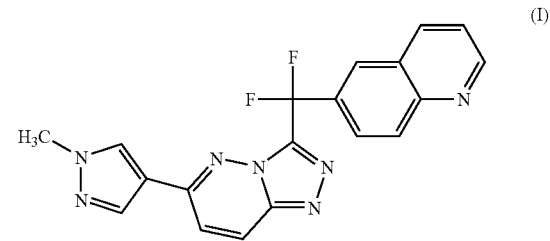 [SMILES: Cn1cc(-c2ccc3nnc(C(F)(F)c4ccc5ncccc5c4)n3n2)cn1]

with an acid provided that the acid is not HCl.

18. The salt of claim 17, wherein said acid is chosen from: HBr, sulphuric acid (H$_2$SO$_4$), trifluoroacetic acid, or a sulphonic acid, preferably p-toluene sulphonic acid, p-bromobenzene sulphonic acid, trifluoromethane sulphonic acid, camphor sulphonic acid, or methane sulphonic acid.

19. A pharmaceutical composition comprising any one or a mixture of the forms of the compound of formula (I) as claimed in any one of claims 10, 12 or 14 to 18 in association with a pharmaceutically acceptable carrier.

* * * * *